(12) United States Patent
Sunnen et al.

(10) Patent No.: US 10,974,019 B2
(45) Date of Patent: Apr. 13, 2021

(54) SYSTEM FOR DELIVERING ULTRA-LOW FREQUENCY (ULF), VARIABLE-INTENSITY, NON-VIBRATORY TACTILE STIMULI FOR REGULATING PHYSIOLOGICAL PROCESSES, AND MODULATING MENTAL STATES

(71) Applicant: PulseWear, LLC, Brooklyn, NY (US)

(72) Inventors: Gerard V. Sunnen, New York, NY (US); Juan Sanabria, Brooklyn, NY (US)

(73) Assignee: PulseWear LLC, Brooklyn, NY (US)

( * ) Notice: Subject to any disclaimer, the term of this patent is extended or adjusted under 35 U.S.C. 154(b) by 0 days.

(21) Appl. No.: 16/424,008

(22) Filed: May 28, 2019

(65) Prior Publication Data

US 2019/0328997 A1    Oct. 31, 2019

Related U.S. Application Data

(63) Continuation of application No. 16/385,851, filed on Apr. 16, 2019, now abandoned.
(Continued)

(51) Int. Cl.
| | |
|---|---|
| *A61M 21/02* | (2006.01) |
| *A61H 23/02* | (2006.01) |
| *A61B 5/04* | (2006.01) |
| *A61B 5/024* | (2006.01) |
| *A61B 5/20* | (2006.01) |

(Continued)

(52) U.S. Cl.
CPC ......... *A61M 21/02* (2013.01); *A61B 5/04012* (2013.01); *A61H 23/0236* (2013.01); *A61B 5/024* (2013.01); *A61B 5/0476* (2013.01); *A61B 5/202* (2013.01); *A61B 2562/0204* (2013.01); *A61B 2562/0219* (2013.01); *A61H 2201/165* (2013.01); *A61N 7/02* (2013.01)

(58) Field of Classification Search
CPC ... A61B 5/04012; A61B 5/024; A61B 5/0476; A61B 5/202; A61B 2562/0204; A61B 2562/0219; A61H 23/0236; A61H 2201/165; A61M 21/02; A61N 7/02
See application file for complete search history.

(56) References Cited

U.S. PATENT DOCUMENTS

| | | | |
|---|---|---|---|
| 2,733,972 A | 2/1956 | Diack | |
| 4,677,756 A * | 7/1987 | Simon | G01B 7/26 33/514 |

(Continued)

FOREIGN PATENT DOCUMENTS

WO    WO 2008/120897    10/2008

*Primary Examiner* — Ojiako K Nwugo
(74) *Attorney, Agent, or Firm* — Leason Ellis LLP

(57) ABSTRACT

Ultra-low frequency (ULF) tactile stimuli, generated by an electro-mechanical actuator, have a spectrum of biological effects. These frequencies are herewith defined as 2 Hz or lower and may comprise stimulus frequencies as low as 0.1 Hz, or one cycle per ten seconds. The ULF generator can be paired with at least one sensor that is configured to monitor a physiological property of the user. A controller is in communication with the at least one electro-mechanical actuator and the at least one sensor and is configured to control operation of the at least one electro-mechanical actuator, in at least a first operating mode, based on measurements of the at least one sensor.

21 Claims, 8 Drawing Sheets

Related U.S. Application Data

(60) Provisional application No. 62/761,994, filed on Apr. 16, 2018, provisional application No. 62/762,886, filed on May 25, 2018.

(51) Int. Cl.
*A61N 7/02* (2006.01)
*A61B 5/0476* (2006.01)

(56) References Cited

U.S. PATENT DOCUMENTS

| | | | |
|---|---|---|---|
| 6,001,073 A | 12/1999 | Schmidt et al. | |
| 6,668,187 B1* | 12/2003 | Porath | A61B 5/0091 |
| | | | 250/358.1 |
| 7,282,036 B2 | 10/2007 | Masuda | |
| 7,510,537 B2 | 3/2009 | Imboden et al. | |
| 8,092,355 B2 | 1/2012 | Mortimer et al. | |
| 9,610,421 B2 | 4/2017 | Sunnen et al. | |
| 2004/0057340 A1* | 3/2004 | Charles-Erickson | G16H 10/65 |
| | | | 368/10 |
| 2005/0043653 A1 | 2/2005 | Trimmer et al. | |
| 2006/0205994 A1 | 9/2006 | Sunnen | |
| 2006/0211958 A1 | 9/2006 | Rosenberg et al. | |
| 2007/0049792 A1* | 3/2007 | Levy | A61H 19/50 |
| | | | 600/38 |
| 2009/0221943 A1 | 9/2009 | Burbank et al. | |
| 2010/0240980 A1* | 9/2010 | Zhu | A61B 5/0022 |
| | | | 600/372 |
| 2011/0179346 A1* | 7/2011 | Dufour | G06F 16/9577 |
| | | | 715/234 |
| 2012/0197093 A1* | 8/2012 | LeBoeuf | G16H 40/63 |
| | | | 600/301 |
| 2012/0238834 A1* | 9/2012 | Hornick | A61B 5/0205 |
| | | | 600/301 |
| 2013/0109914 A1* | 5/2013 | Imboden | A61H 23/0218 |
| | | | 600/38 |
| 2014/0031895 A1* | 1/2014 | Rahimi | A61N 1/36021 |
| | | | 607/46 |
| 2014/0135592 A1* | 5/2014 | Ohnemus | A61B 5/0022 |
| | | | 600/301 |
| 2014/0192626 A1* | 7/2014 | Wolff | G04G 21/08 |
| | | | 368/63 |
| 2015/0364022 A1* | 12/2015 | Dyell | G16H 40/63 |
| | | | 340/573.1 |
| 2015/0366518 A1* | 12/2015 | Sampson | A61B 5/0478 |
| | | | 600/301 |
| 2016/0019458 A1* | 1/2016 | Kaufhold | G01S 7/417 |
| | | | 342/25 F |
| 2016/0029939 A1* | 2/2016 | Ouwerkerk | A61B 5/02405 |
| | | | 600/301 |
| 2016/0066837 A1* | 3/2016 | Melo | G09B 5/00 |
| | | | 600/549 |
| 2016/0080888 A1* | 3/2016 | Kreitzer | G06F 3/017 |
| | | | 455/39 |
| 2016/0089081 A1* | 3/2016 | Morris | A61B 5/04085 |
| | | | 600/384 |
| 2016/0109953 A1* | 4/2016 | Desh | A44C 5/0007 |
| | | | 345/169 |
| 2016/0143554 A1* | 5/2016 | Lim | A61B 5/6814 |
| | | | 600/383 |
| 2016/0150987 A1* | 6/2016 | Kwon | A61B 5/04012 |
| | | | 600/476 |
| 2016/0155309 A1* | 6/2016 | Watson | A61B 5/7282 |
| | | | 600/324 |
| 2017/0042433 A1* | 2/2017 | Noh | A61B 5/02108 |
| 2017/0112452 A1* | 4/2017 | Otto | G16H 50/30 |
| 2017/0147775 A1* | 5/2017 | Ohnemus | G16H 10/20 |
| 2018/0020931 A1* | 1/2018 | Shusterman | A61B 5/02125 |
| | | | 600/483 |
| 2018/0035297 A1* | 2/2018 | Cronin | H04L 63/105 |
| 2018/0055441 A1* | 3/2018 | Candy | A61B 5/742 |
| 2018/0096583 A1* | 4/2018 | Chen | A61B 5/0205 |
| 2018/0103859 A1* | 4/2018 | Provenzano | A61B 5/0816 |
| 2018/0184920 A1* | 7/2018 | Rabinovich | A61B 5/681 |
| 2018/0184923 A1* | 7/2018 | Tal | G01L 9/06 |
| 2019/0076077 A1* | 3/2019 | Baggen | A61B 5/7475 |
| 2019/0110757 A1* | 4/2019 | Kwon | A61B 5/021 |
| 2019/0328294 A1* | 10/2019 | Foresto | A61B 5/7455 |
| 2019/0343454 A1* | 11/2019 | Suokas | A61B 5/1116 |

\* cited by examiner

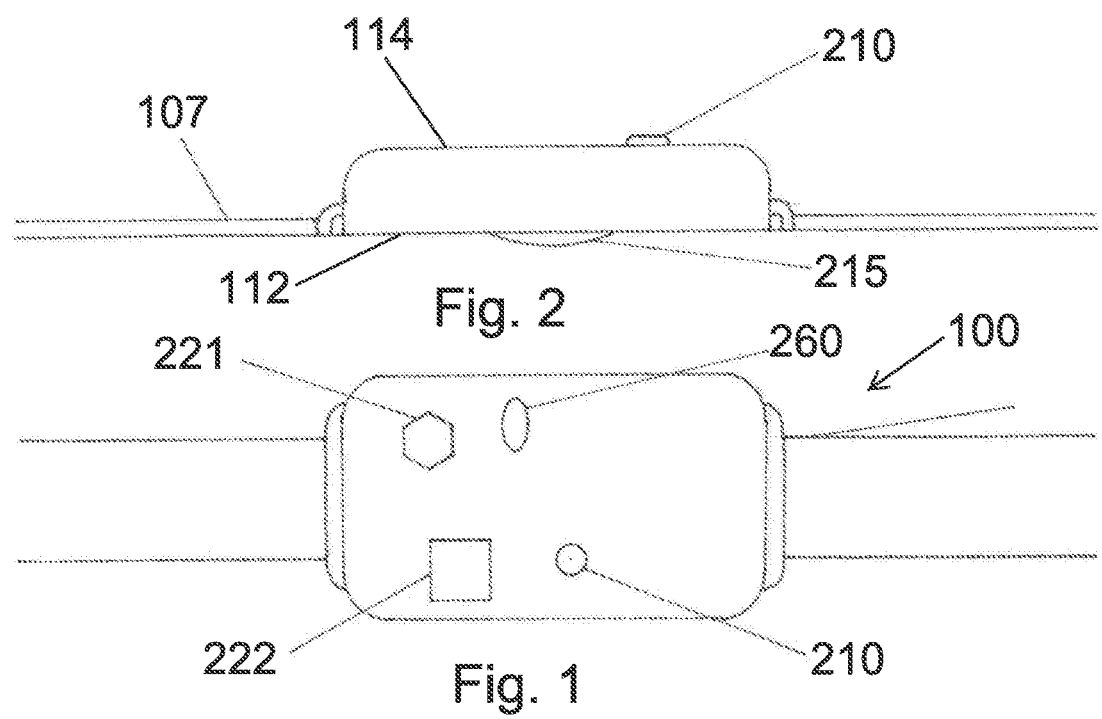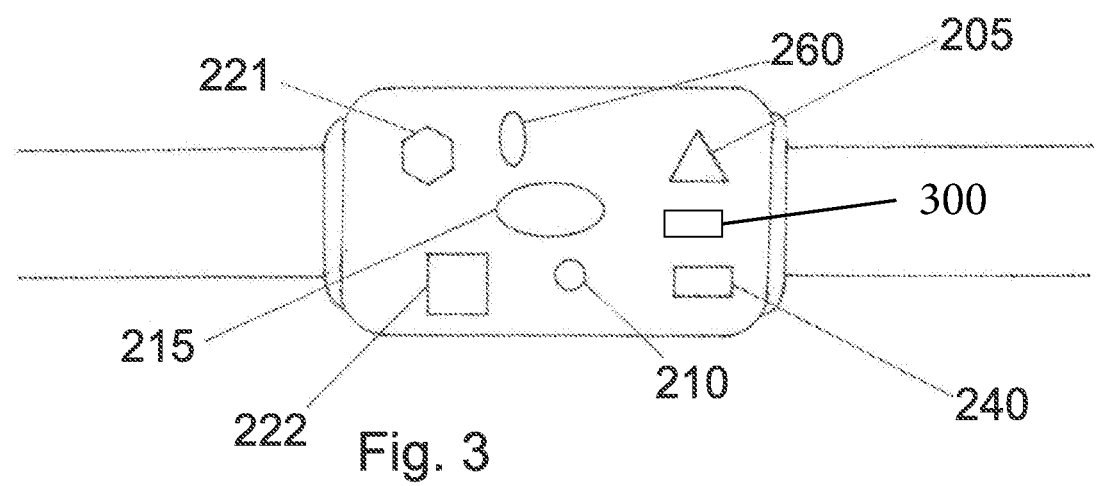

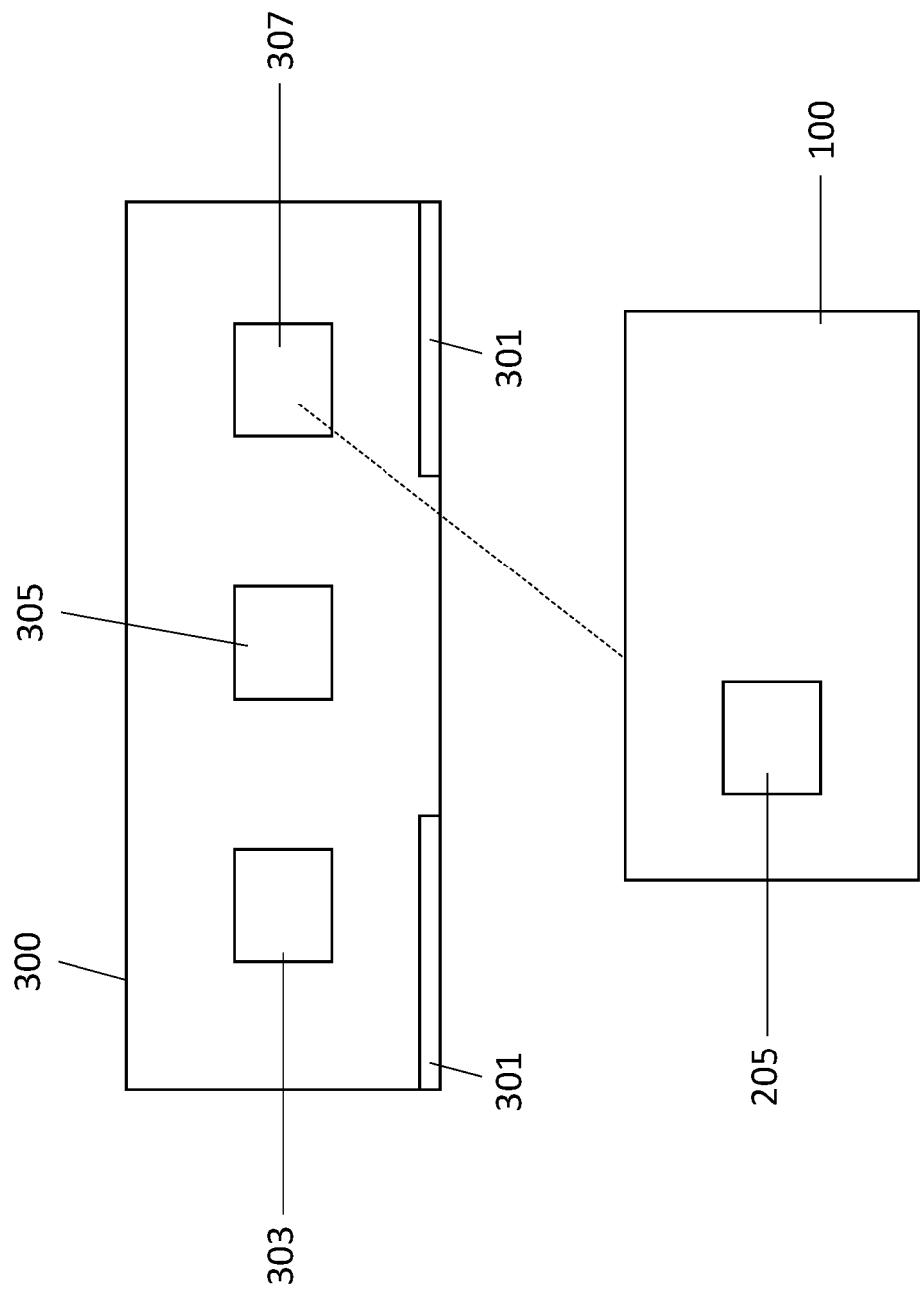

US 10,974,019 B2

SYSTEM FOR DELIVERING ULTRA-LOW FREQUENCY (ULF), VARIABLE-INTENSITY, NON-VIBRATORY TACTILE STIMULI FOR REGULATING PHYSIOLOGICAL PROCESSES, AND MODULATING MENTAL STATES

CROSS-REFERENCE TO RELATED APPLICATIONS

This application is a continuation-in-part of U.S. patent application Ser. No. 16/385,851, filed Apr. 16, 2019, which is based on and claims priority to U.S. Provisional Patent Application 62/761,994, filed Apr. 16, 2018, and this application is also based on and claims priority to U.S. Provisional Patent Application 62/762,886, filed May 25, 2018, the entire contents of each of which is incorporated by reference herein as if expressly set forth in its respective entirety herein.

BACKGROUND

Physiological processes are commonly defined as being the functions and activities of living organisms that support life in single- or multi-cellular organisms from their origin through the progression of life. As one would appreciate there are a number of different physiological processes and there is a desire in a number of different settings to control the regulation of such physiological processes. Such physiological processes can include but are not limited to:
1. The slowing of brain waves
2. The induction of relaxation and sleep
3. The lowering of blood pressure
4. The slowing of heart rate
5. The normalizing of gastro-intestinal peristalsis
6. The pacing and slowing of respiratory rate
7. The modulation of urinary bladder over-activity
8. The alleviation of muscular system over-activity While there have been attempts to control and regulate such physiological processes, there remains a need to provide alternative devices and methods for regulating such physiological processes.

SUMMARY

An apparatus (ultra low frequency (ULF) device) is provided and is configured to generate and apply mechanical stimuli to skin of a user for regulating a physiological process. The apparatus includes a housing having a first surface for placement against the skin and further includes at least one electro-mechanical actuator provided along first surface and configured to generate and apply the mechanical stimuli to the skin. The mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived. The apparatus also includes at least one sensor that is configured to monitor a physiological property of the user.

A controller is in communication with the at least one electro-mechanical actuator and the at least one sensor and is configured to control operation of the at least one electro-mechanical actuator, in at least a first operating mode, based on measurements of the at least one sensor. In one embodiment, the one or more sensor is selected from the group consisting of: (1) a first sensor for detecting bodily motion; (2) a second sensor for detecting electro-dermal activity; (3) a third sensor for detecting body temperature; (4) a fourth sensor for detecting a pulse rate; (5) a fifth sensor for detecting respiratory rate; (6) a sixth sensor for measuring gastro-intestinal activity; and (7) a seventh sensor for measuring bladder activity.

In yet another embodiment, an apparatus configured to generate and apply mechanical stimuli to skin of a user for regulating a physiological process. The apparatus includes a flexible headband having a first surface for placement against the skin of a head of the user and at least one electro-mechanical actuator provided along first surface and configured to generate and apply the mechanical stimuli to the skin. The mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived. At least one sensor is configured to monitor a physiological property of the user and comprises an electroencephalogram (EEG) sensor; and a controller that is in communication with the at least one electro-mechanical actuator and the at least one sensor for controlling operation of the at least one electro-mechanical actuator, in at least a first operating mode, in view of measurements of the EEG sensor. The controller is configured to deliver the mechanical stimuli when at least a threshold percent of recorded wave frequencies are Beta waves, having wave frequencies from about 12 Hz to about 30 Hz, as opposed to Alpha waves, having wave frequencies from about 8 Hz to about 12 Hz.

The present refinement proposes such feedback capabilities relative to cardio-pulmonary functions. Specialized sensors relay information to the ULF device on physiological data relevant to heart function that may include:
Data for pulse rate
Data for respiratory rate
Data for blood pressure.
Data for blood oxygen saturation Although the above are the main physiological data electively received by the ULF device, other data may offer helpful information relative to cardiovascular function, namely:
Data for electro-dermal activity (EDA)
Data for electroencephalographic activity (EEG).
Data for bodily motion and movement
Data for skin and body temperature
Data for muscular tension.

Predicated upon any one or several of the above sensors' data, the ULF device may be activated and modulated to lend its pan-systemic relaxing signals for the normalization of cardio-pulmonary functions.

The innovations proposed center on the normalization of cardiovascular and cardio-pulmonary functions via the use of sensors, communicating with microprocessors that drive actuators to establish harmony in vegetative bodily functions regulated by the Autonomic Nervous System.

BRIEF DESCRIPTION OF DRAWING FIGURES

FIG. 1 is a top plan view of a device in accordance with one exemplary embodiment of the present invention and configured to generate ultra-low frequency non-vibratory tactile stimuli for the regulation of physiological processes;

FIG. 2 is a side elevation view thereof;

FIG. 3 is a cross-sectional view thereof;

FIG. 7 is a schematic of an exemplary GSR/EDA sensor in communication with the ULF device.

DETAILED DESCRIPTION OF CERTAIN EMBODIMENTS

Figure 4:
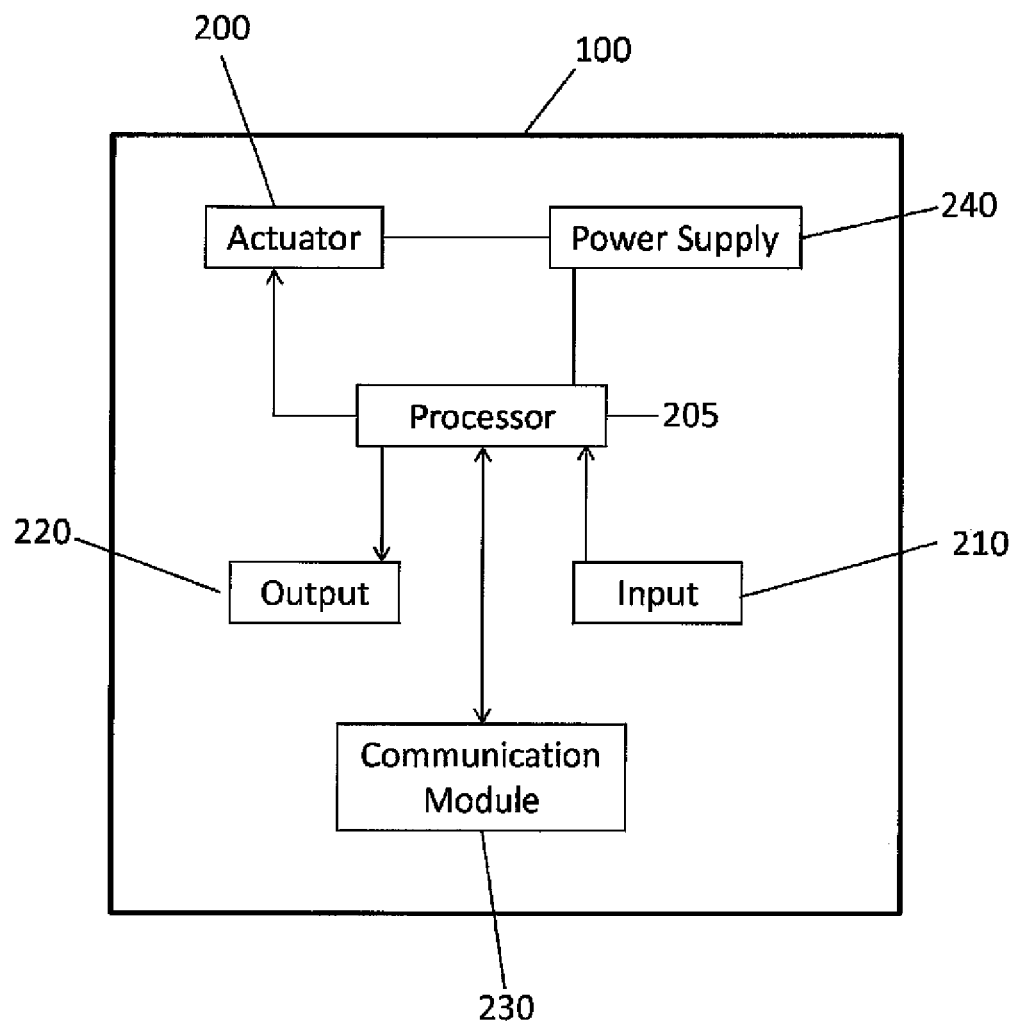
FIG. 4 is a block diagram showing the various components of the device of the present invention.

Applicant cites to their own prior work including U.S. Pat. No. 9,610,421 B2 "Devices and Methods Utilizing Ultra-Low Frequency Non-Vibratory Tactile Stimulation for Regulation of Physiological Processes; and Canada: Serial No 2,733,972 "Vibrational Delta and Theta Brain Wave Induction Apparatus and Method for Stimulation of Sleep," each of which is hereby expressly incorporated by reference in its entirety. In addition, a US patent application U.S. Ser. No. 11/075,075 was submitted in 2005 and entitled, "Vibrational Delta and Theta Brain Wave Induction Apparatus and Method for the Stimulation of Sleep," which is hereby expressly incorporated by reference in its entirety.

System for ULF Generator (Device)

In at least one aspect, the present invention is directed to a system 10 that incorporates one or more devices 100 that generate controlled stimuli and more particularly, the devices 100 are directed to those devices that generate ultra-low frequency (ULF) tactile stimuli and thus, the devices can be referred to herein as "ULF devices" or "ULF actuators". Ultra-low frequency (ULF) tactile stimuli have biological effects. These frequencies are herewith defined as 2 Hz or lower and can comprise stimulus frequencies as low as 0.1 Hz, or one cycle per ten seconds according to at least one embodiment.

The present invention teaches the presentation of ultra-low frequency rhythmic or paced stimuli to the skin which are, according to definitions of vibration, not vibratory, because they neither have a periodic motion, nor do they have a point of equilibrium. Moreover, they are of such low frequency that they lie below the lower ranges for what is commonly conceived as vibrational.

Although the pulses delivered by ULF devices are non-vibratory, each individual pulse may consist of short bursts of vibrational energy. The important distinction is that the pacing of the individual pulses respects ultra-low frequency ranges. A single pulse will not be experienced as a vibration, but rather as a single stimulus. Each single pulse may thus be created by vibrational energies that may include levels referred to as sub-sonic (1 to 20 Hz), sonic 20 to 20 kHz), or ultrasonic, namely that which reaches beyond human hearing (greater than 20 kHz); or also within the range of medical ultrasound: 1 to 20 MHz.

Some of the physiological processes influenced by ultra-low frequency stimulation find themselves in the province of the capacities of the device 100 herewith described and include, but are not limited to:

Some of the physiological effects produced by ultra-low frequency (ULF) stimulation find themselves in the province of the capabilities of the device 100 herewith described and include, but are not limited to:

The slowing of heart rate

The appeasement of blood pressure

The slowing and pacing of respiratory rate

The increase in blood oxygen saturation

The slowing of brain waves

The induction of relaxation and sleep

The alleviation of hyperactivity/attention deficit conditions

Stress reduction

The normalizing of hyperactive gastro-intestinal peristalsis

The modulation of urinary bladder over-activity

The alleviation of muscular system over-activity

The devices described in the above granted patents deliver tactile stimuli by means of solenoids or transducers that actuate membranes or diaphragms apposed to skin. These in turn are powered by battery sources, and are controlled by microprocessors.

The present device 100 has feedback capabilities relative to cardio-vascular functions. Specialized sensors relay information to the ULF device on physiological data relevant to heart function that may include several measures of cardio-vascular activity.

The present device further can have modulation and normalization of cardiovascular parameters such as heart rate, blood pressure, respiratory rate and blood oxygen saturation via sensors that communicate with the ULF devices. The invention works, in one embodiment and broadly, as follows:

1. Sensors measuring pulse rate—and/or blood pressure, respiratory rate, and blood oxygen saturation—communicate with ULF device microprocessors.
2. Predicated on the data received, said microprocessors may opt to drive actuators that impart tactile and other messages to the nervous system via ultra-low frequency (ULF) stimuli, herewith defined as 2 Hz to 1/10 Hz (one stimulus every ten seconds).
3. Said messages imparted to the nervous system by ULF devices modulate and normalize cardio-vascular-pulmonary functions by their capacity to:
4. Lower pulse rate
5. Reduce blood pressure
6. Pace respiratory rate and increase gas exchange
7. Enhance blood oxygen saturation The Anatomy of Physiology of Sensor Mechanoreceptors The device 100 apposed to the skin surface stimulates the sensory organs of the peripheral nervous system. The skin generates a constant flow of information, forwarding it to the spinal cord and to the central nervous system for quasi-instantaneous processing and response. Sensing the shape, temperature, and motion of movements requires skin sensors that quickly translate mechanical energy in the environment into neurological signals.

Skin sensors are micro-organs that inform on texture, pressure, impact, heat, cold, vibration and, importantly, on tissue trauma and inflammation. For the latter, they generate pain signals. Beyond the skin itself, in deeper connective tissues of muscles, tendons and joints, other micro-organs (e.g., spindles) also convey neurological information on body position and motion.

Several types of sensors found in the human skin and in deeper tissues provide a remarkable array of instantaneous information about many of the environment's variegated features:

1. Pacinian corpuscles, found in the dermis, are large by sensor standards and visible to the naked eye. Histologically, they appear as onion-configured concentric lamellae of connective tissue housing unmyelinated nerve roots. The friction of rubbing a finger on a textured object will induce vibratory stimuli registered by Pacinian corpuscles. Their fast adaptation makes them ideal for registering transient touch. Endowed with a large receptive field on the skin surface, they are sensitive to a range of vibrations of 15 to 400 Hz, with an optimal response at approximately 250 Hz.
2. Meissner's corpuscles are encapsulated dermal skin sensors endowed with unmyelinated nerve roots whose adaptive capacities make them optimally responsive to vibrations 50 Hz and below.
3. Merkel's discs respond to minuscule distortions of tissues. Uncapsulated, unmyelinated and extremely sensitive, they are capable of kind of tactile high resolutions needed in Braille. Their optimal vibrational responsiveness ranges between 5 and 15 Hz.
4. Krause's bulbs are minute cylindrical bodies found in superficial skin layers and mucosal tissues. They respond to cold and to low frequency vibrations.
5. Ruffini cylinders are capsulated spindle-shaped receptors found in deeper skin layers. Heat and low frequency vibrations stimulate them.
6. Free nerve endings are unmyelinated neurons abundantly found in the epidermis that transmit signals eventually interpreted as pressure, and pain in any one of its many variations.

The speed of nerve transmission from skin sensors to the spinal cord, and eventually to the brain, depends on the diameter of conducting nerve fibers and on the degree to which they are sheathed in myelin, an insulating complex lipid. The highly myelinated A fibers are large neuronal cables with conduction velocities of 70 to 120 meters/second. They carry sensation of proprioception, touch and pressure. C fibers, on the other hand, thin and unmyelinated, have conduction velocities approximating 1 meter/second. They carry pain sensations.

Sensory fibers with various conduction velocities conveying qualitatively different messages converge to the dorsal columns of the spinal cord, where they ascend to the medulla oblongata, the pons, the midbrain, and on to the thalamus. There, raw sensations gain conscious perception. Thalamic projections forward data to the cortex, where sensations are given subtleties.

Ultra-Low Frequency Stimuli and Physiological Functions

The stimuli generated by the ULF device 100 can be perceived consciously and/or subliminally. Via focused attention, visualization and meditation, this perception may be directed to the organ system in need of modulation. Thus, the stimuli may:

Influence brain wave frequency. In the present invention, the device aims to reduce brain wave frequencies in order to promote relaxation and sleep.
Reduce blood pressure and stabilize heart rate.
Harmonize gastro-intestinal function via the slowing of gastro-intestinal peristalsis.
Stabilize and slow respiratory rate.
Promote muscular relaxation.
Regulate genito-urinary function (slowing bladder activity).
Easing the activity of muscular systems, including the voluntary system (striated muscles), and the autonomic system (smooth muscles).

Slow Brain Waves

ULF topical stimuli may be used to coax brain waves to lower their frequencies. Slow brain waves (SBW) are associated with a large number of physiological, biochemical, and psychological changes, namely:

Relaxation and sleep
Stabilization of blood pressure.
An elevation of mood
Memory consolidation
Improved daytime performance.
Improved glucose metabolism.
Increased cerebral protein synthesis
Increased production of brain gamma-amino butyric acid (GABA)
The production of nitric oxide by certain cortical neurons.
Increased output of pituitary growth hormone
Increased Growth Hormone (GH) output.
Maturation of the cortex during adolescence.
The production of cytokines, thus bolstering immune function.

The physiological, biochemical, and psychological parameters that are influenced by slow brain waves are therefore numerous and diverse and comprise much more than sleep induction.

The present invention has the capacity to slow down a constellation of bodily processes that include not only brain waves but also cardiovascular, respiratory, gastro-intestinal, muscular, and genito-urinary functions.

The ULF device 100 herewith presented generates repetitive, paced ultra-low frequency tactile stimuli. These tactile stimuli travel within the nervous system, resonating in neural networks, which in turn influence brain pacemakers. Reaching a desired brainwave frequency in a more expeditious way is made possible by presenting the subject with stimulus frequencies much lower than the desired target brainwave frequency. For example, if the target brainwave frequency is 1 Hz, a Delta brainwave associated with sleep, the subject may be presented with a repetitive 0.2 Hz frequency, or one stimulus per 5 seconds. This signals brain sleep pacemakers to activate their innate tendency for synchronicity.

One objective of this device is to entrain cardiovascular function to adopt normal parameters of blood pressure and heart rate. The range of the cardiac device's output spans from 1 Hz, or one cycle per second (reflecting a normal healthy heart rate of 60 beats per minute), to 0.2 Hz, or one stimulus per 5 seconds, which coaxes heart rate to normalize more quickly. Optimally, heart rate is most desirable in the range of 55 to 65 beats per minute.

In order to send ultra-low frequency signals to the brain's networks, the device 100 may be positioned on the wrist as a wristband, or on the head, as a headband. In the latter option, the device's solenoid actuator may be placed on selected points on the skull.

Pulse Rate Regulation

Many interactive mechanisms determine the circuitry of the autonomic nervous system in its regulation of heart rate and blood pressure.

Baroreceptors are sensors located in the walls of vessels that respond to stretching. As vessels dilate, baroreceptors emit signals that make their way to the medulla oblongada in the brain stem from there, via autonomic nervous system fibers, signals adjust heart rate, cardiac output, blood pressure, and vascular resistance. Other mechanisms involve neuro-humoral networks, the adrenal glands, and the renin-angiotensin system.

The medulla, with its extensive connections to sympathetic and parasympathetic circuits, contains nuclei that also regulate respiration and the reflexes of coughing, pupillary adjustment, salivation, sneezing, swallowing, vomiting, and intestinal movements.

The reticular formation, within the medulla and throughout the brain stem and midbrain, is a yet relatively unexplored massive conglomeration of neurons that, under the microscope, appears as a net (reticulum: net (Greek). The reticular formation receives signal from all body sensors and, importantly, from the most differentiated brain centers, namely the cortical areas, generators of the highest expressions of consciousness.

The medulla's nuclei act as automatic servomechanisms. However, the fact that cortical centers of perception, consciousness and volition have connections to the reticular formation and thus to the medullar networks signifies a role for the conscious control of heart rate and blood pressure, which this device is designed to develop.

Modulating Hypertension

Hypertension poses enormous public health issues. Chronic high blood pressure is well known to be associated with heart attacks (myocardial infarctions), strokes, peripheral vascular disease, kidney disease (nephropathy), and retinal pathology (retinopathy).

Hypertension treatment is best provided using a total patient approach. In this model, all factors affecting high blood pressure are examined and treatment is applied accordingly. A total health assessment looks at all organ systems and, importantly, on lifestyle factors (e.g. dietary and sleep habits, drug and alcohol use, etc.). Medication therapy is usually combined with prescriptions for lifestyle modification. High blood pressure has also been treated with adjunctive psychological techniques including relaxation training, psychotherapy, meditation, hypnosis, and biofeedback.

The present invention proposes a device 100 and method for modulating blood pressure and regulating heart rate, utilizing stimuli that entrain the nervous system toward more peaceful rhythms. Said stimuli are tactile. They, however, can be assisted by the support of auditory, visual, and electrophysiological stimuli. The invention's fundamental concept is that paced ultra-low frequency tactile stimuli have the capacity to regulate, via its reverberating nervous system circuitry, the rhythm of the heart, and the tonicity of the body's vasculature.

The invention's rationale is based on the anatomical fact that neurological circuits extensively cross-communicate. A unifying principle applicable to the nervous system is that every neuron in the body finds connections to every other neuron. This principle is one foundation of this invention. Specifically, a stimulus applied to the skin, will travel throughout nervous system networks, eventually resonating into all cortical and subcortical structures, including the heart rate and blood pressure centers in the nervous system's medulla and brain stem.

The objective of this device 100 is to entrain cardiovascular function to adopt normal parameters of blood pressure and heart rate. The range of the cardiac device's output spans from 1.5 Hz, (reflecting the higher range limits of normal heart rate, namely 90 beats per minute), to 0.2 Hz, or one stimulus per 5 seconds, which coaxes heart rate to normalize more quickly. Optimally, heart rate is most desirable in the range of 55 to 65 beats per minute.

The apparatus (device 100) and method can also be augmented with synchronous auditory, visual, and electrophysiological stimulation. Multimodal stimuli increase the capacity of the apparatus to regulate the blood pressure and heart rate centers in the nervous system via the involvement of other nervous system pathways and networks.

The device's effectiveness is enhanced by techniques of concentration, visualization and meditation. By lending mindful attention to the experiencing of the device's output, the reprogramming of the nervous system is accelerated, and cardiovascular control is more efficiently achieved.

Regulating Gastro-Intestinal Function

The normal function of the intestinal conduit is associated with rhythmic peristaltic waves of smooth muscle contractions spanning its entire length. These waves are essential for the proper transit and digestion of food. Peristaltic contractions in the esophagus allow food boluses to travel to the stomach, and their waves travel the length of the esophagus approximately every 9 seconds, at velocities of some one inch per second.

In the intestines, peristaltic movement is similarly slow and rhythmical. In abdominal distress due to simple indigestion, peristaltic movements are often accelerated. The device proposed herewith, sends ultra-low frequency stimuli to the abdominal viscera, thus signaling smooth muscles to regulate their pace. In this manner, intestinal harmony is more actively achieved than if simply left alone without prompting.

In this configuration, the device is apposed to the abdomen via a belt. The range of stimuli frequencies appropriate to this task approximates 0.5 Hz or one impulse per 2 seconds to 0.1 HZ, ((or lower to encourage prompting).

The device's effectiveness is enhanced by techniques of concentration, visualization and meditation. By focusing mindful attention on the experiencing of the device's output, the reprogramming of the visceral nervous system is accelerated, and gastro-intestinal harmony is more efficiently achieved.

Regulating Neuro-Muscular Activity

Muscles and joints that have been stressed are physiologically over-active and are prone to emitting higher intensities and frequencies of electrical muscle activity.

The ULF device 100 emits ultra-low frequency stimuli imparted to the muscles via direct apposition to the skin surface. The ULF sensory signals imparted by the proposed device act to appease the over-activity of the said muscles, by coaxing their firing rates to more subdued levels.

The device's effectiveness is enhanced by techniques of concentration, visualization and meditation. By focusing mindful attention on the device's output, the down-regulation of the neuro-muscular nervous system is accelerated.

Stimulus Characteristics and Configurations

The following feature and claims describe tactile stimuli configured to elicit selected mechanoreceptor skin responses. In addition, claims are made for the portion of the device that actually apposes itself to the skin surface of the subject, the interface. The present invention privileges the creation of tactile stimuli that are adapted to the physiology of the human skin, and to the properties of the nervous system, namely entrainment and coaxing.

Stimuli are imparted to skin tissues with varying degrees of energy. At lower settings, the force pressure is stimulating to a limited number of mechanoreceptors, mostly located in skin's surface layers. At higher pressure settings, it exerts influence on deeper connective tissues, muscles and joints.

Light pressures, as in the first case, may be as low as 1 Gm/cm2; while in the second case, pressure may reach 250 Gm/cm2.

Lateral force measurements are important in stimuli that have horizontal movements. Force pressure is applied to the stimulus motion in order to displace tissues laterally. Lateral movements stimulate receptors containing mechanoreceptors sensitive to sideway motions. Horizontal displacement optimal for human skin spans from 1 mm to 1 cm.

The device is capable of generating vertical and horizontal stimuli. This allows for the stimulation of mechanoreceptors whose nerve roots respond to vertical, and horizontal compression. The amplitude displacement of these vertical pulses optimal for human skin may span from 0.5 mm to 5 mm. The device may be capable of circular motions, which offers mechanoreceptor stimulation in horizontal planes, or sinusoid movements, which creates mechanoreceptor stimulation in all vertical and all horizontal planes.

The interface element of the device may be made of materials that maximize touch receptor stimulation. Sensory loading and neural recruitment are thus augmented.

Physiological Principles of the ULF Device

The physiological principles underlying the ULF device 100 include entrainment, coaxing, pacing and synchronicity.

Entrainment

The ULF device 100 calls mainly on the principle of entrainment for modulating physiological processes. Using this concept for slowing the frequency of brain waves, for example, a stimulus frequency is applied corresponding to a desired brain wave frequency. If a subject's brainwaves were currently measured at 10 Hz and the goal was to lower them to 5 Hz, the subject would be presented with a 5 Hz stimulus frequency and, via entrainment, there would hopefully be, in time, a correspondence of stimulus to brain wave (e.g., brainwaves would approach 5 Hz).

Applied to the cardiovascular system, in a detected pulse rate of 100 per minute—the threshold for tachycardia—the ULF device would deliver a stimulus frequency of 70 per minute, an ideal pulse rate. Via entrainment and time, the pulse rate would be invited to attain this more coveted level.

Coaxing

In addition to entrainment, the present invention makes use of another physiological mechanism that can be called "Coaxing." In this phenomenon, a stimulus may be presented with a lower frequency than the desired physiological response, so that the said desired response is attained more quickly.

Pacing

Pacing is a third mechanism. In pacing, the property of rhythmic presentation of the stimulus is invoked. The pacing of the stimuli is such that, with ongoing repetition, more and more neuronal networks join in tandem firing, thus providing for a stronger stimulus force.

Synchronicity

Synchronicity is invoked, as a phenomenon that, in addition to pacing, invites an ever-greater population of brain neurons to fire in unison.

Exemplary Configurations of the Device

The devices 100 can take several forms and configurations including the following configuration which comprises a non-limiting list of exemplary configurations.

1. A wristband. The components of the device, namely the microprocessor, the battery and the actuator are integrated into a wristband. Designed for nervous system stimulation via the wrist.
2. A headband. The device is integrated into a headband designed to provide contact of the actuator to the head's skin surface (FIG. 8A).
3. An ankle bracelet. The ankle bracelet works much like the wristband but is worn on the ankle.
4. A belt. The belt configuration provides contact of the actuator with abdominal skin.
5. The chest band allows the ULF device to sense respiratory rate via the inclusion of accelerometers.
6. The device may be incorporated into a pillow in which the ULF device is located along one pillow surface (FIG. 8B).

As mentioned above, in one mode of utilization, the device 100 may be attached to the wrist, the ankle, the head, or to the abdomen as in a belt configuration. Eyes closed, the patient gently centers attention on the stimuli produced by the device.

The individual wishing to drift to sleep allows the cadence of the stimuli to coax brainwaves into a progressive slow-down. As described herein, a timer function allows for a 15-minute session during which time sleep may have occurred. With repeated use, the device's signals come to represent conditioned reflexes for sleep onset. As described herein, a user interface can be used to set up and then turn on/off the timer function. The user can select and input the session time (e.g., time in minutes).

The individual wishing to normalize heart rate and blood pressure may choose to take readings before using the device. The device is set at a frequency and amplitude that is indicated by a chart, predicated on the readings.

The system 10 further includes one or more sensors 300 whose readings (measurements) can be shown on a display along with other information, such as selecting operating mode and parameters inputted into the user interface. Certain models may display brain wave frequencies.

The device's effectiveness is enhanced by techniques of concentration, visualization and meditation. Focusing mindful attention on the experiencing of the device's output enhances the reprogramming of the nervous system; relaxation and sleep functions, cardio-vascular, muscular, and gastro-intestinal harmony are more efficiently achieved.

Consistent use of the device will, in time, lead to the establishment of conditioned reflexes that elicit the desired responses more quickly and automatically. The sleeper, for example, may find that his or her sleep onset time is greatly shortened with dedicated use of the device.

Exemplary ULF Device Construction

FIGS. 1-4 show one exemplary device 100 according to one exemplary embodiment of the present invention. As described herein, the device 100 can take any number of different forms depending upon different considerations, such as anatomical considerations. In general, the device 100 is configured for placement at a target location of a patient to ensure the proper intimate contact between the device 100 and the skin of the person. The device 100 can thus be of a type that can be detachably attached to the person using any number of different coupling techniques, such as using a mechanical fastener (e.g., the illustrated straps in the figures) or using adhesives (e.g., constructing the device 100 in the form of a patch that has an adhesive section (such as a border) for attachment to the skin of the person or using other suitable techniques or can be incorporated into an article, such as clothing, that can be worn. As shown in FIGS. 1-4, the device 100 includes a housing or casing 110 which contains the operative parts of the device 100 and includes a fastener (fastening means) for attaching the device 100 to a person's body (patient's body). In the exemplary embodiment shown in the figures, the device 100 takes the form of a wearable structure, such as a bracelet or the like, and the fastener can be in the form of a pair of straps 107 that engage and mate together so that the device 100 is positioned and maintained at a target location of the person's body. For example, the straps 107 can include conventional buckles or hook and loop material to allow the straps 107 to engage one another and allow the device 100 to be fastened about the person's body (e.g., about a limb).

The housing 110 can take any number of different shapes and sizes depending upon the particular intended application. For example, the housing 110 can have a regular shape, such as a circle, square, oblong shape, rectangular or can have an irregular shape. Other constructions of the housing 110 are described herein.

The housing 110 includes a first face or surface 112 and an opposing second face or surface 114. The first face 112 can be thought of as a lower surface which is a skin contacting surface and the second face 114 can be thought of as being a top surface that faces away from the skin.

As discussed herein, the first face 112 can be formed of more than one material and/or contain more than one section and in particular, the first face 112 can have an active section 215 that is intended to be placed in direct contact with the skin of the person. The active section 215 can be formed of a different material that allows for transmission of the ultra-low frequency stimuli to the skin in the manner described herein and also provides a comfortable interface for the skin. For example, the active section 215 can be formed of a membrane that is formed of a suitable material that freely allows transmission and delivery of the ultra-low frequency stimuli generated by the device 100.

The housing 110 can be formed of any number of suitable materials, including various plastics.

The device has a number of other components, such as a user interface and display and controls as well as a power supply and a means for generating the ultra-low frequency stimuli. Each of these components and others is described in detail below.

In accordance with the present invention, the ultra-low frequency device 100 makes use of the principle of entrainment for modulating physiological processes. Using this concept for slowing the frequency of brain waves, for example, a stimulus frequency is applied corresponding to a desired brain wave frequency. If a subject's brainwaves were currently measured at 10 Hz and the goal was to lower them to 5 Hz, the subject would be presented with a 5 Hz stimulus frequency and, via entrainment, there would hopefully be, in time, a synchronous correspondence of stimulus to brain wave. The foregoing is merely one exemplary application and not limiting of the invention.

In the present invention, the principle developed is what could be called and understood, in addition to entrainment, physiological coaxing and pacing. In this phenomenon, a stimulus may be presented with a much lower frequency than the desired physiological response, so that the said desired response is attained more quickly. While stimuli are generally presented at regular intervals, the present invention also makes possible the presentation of stimuli at irregular or at patterned frequencies. As discussed herein, the user interface associated with the device 100 allows the user to select the operating mode of the device 100 and this can include the manner in which the stimuli are applied (e.g., at what intervals are the stimuli applied). In addition, the user interface can be used to select different operating modes of the ULF device 100, such as a sleep mode or normal operating mode. During sleep mode, the ULF device adjusts the ranges of activity that would be expected during a sleep session (e.g., the amount of bodily movement during sleep is dramatically less than during the day, etc.).

The method of delivery for these ultra-low frequency stimuli can be via electro-mechanical devices that incorporate solenoids. The properties inherent in this technology is that solenoids have the capacity to generate ultra-low frequency repetitive stimuli, rhythmical or not, while other methods, including those that rely on rotating motors to produce vibrations, cannot. Solenoid electromagnetic technology, for example, can thus deliver impulses to the body that range far below the Delta brain wave frequencies, the lower limit of Delta being 0.5 Hz. The impulses generated by solenoid technology can be programmed to frequencies as low as 0.1 Hz (or one stimulus every 10 seconds), and lower.

FIGS. 1-3 illustrate one exemplary ultra-low frequency (ULF) device 100 and FIG. 4 is a block diagram illustrating an exemplary configuration of the device 100 according to an embodiment of the present invention. The device 100 includes various hardware and software components that serve to provide ULF stimuli to a user. The ULF device 100 includes, inter alia, a microprocessor 205 that is communicatively coupled, to a solenoid (or transducer) 200, one or more input devices 210 (e.g., control button and/or touch interface), one or more output devices 220 (e.g., an LED 221 and/or LCD display 222) and a communication interface 230. The ULF device also includes a power source 240 that serves to provide energy to the various components of the device 100, as would be understood by those in the art.

The output device can include a speaker 260 which is configured to emit sound. The rhythm frequency can, in addition to tactile stimuli, generate anyone of a number of sounds, or tones. A menu of pleasing sounds may be chosen (as by means of the user interface (input device)) such as waterfalls, waves, musical instruments, or electronically generated sounds.

The microprocessor 205 is configured to control the various components of the ULF device 100 and carry out aspects of the systems and methods disclosed herein. The microprocessor 205 can be a number of processors, a multi-processor core, or some other type of processor, depending on the particular implementation. In some implementations the microprocessor 205 is configured by executing one or more software modules that can be loaded into a memory (not shown) and executed by the microprocessor 205. The one or more software modules can comprise one or more software programs or applications having computer program code or a set of instructions executed in the microprocessor 205. Such computer program code or instructions can be written in any combination of one or more programming languages. Preferably, included among the software modules are a user input module, a display module, a stimuli control module and a communication module. During execution of the software modules, the microprocessor 205 configures the ULF device 100 to perform various operations relating to providing ULF stimuli to the user, as will be described in greater detail below.

Memory can be, for example, a random access memory (RAM) or any other suitable volatile or non-volatile computer readable storage medium. In addition, memory can be fixed or removable and can contain one or more components or devices such as a hard drive, a flash memory, a rewritable optical disk, a rewritable magnetic tape, or some combination of the above. In addition, memory can be onboard the microprocessor. In addition, it should be noted that other information and/or data relevant to the operation of the present systems and methods can also be stored on memory, as will be discussed in greater detail below.

The electromechanical solenoid 200 is also operatively connected to the microprocessor 205 (as mentioned, the element 200 can alternatively be an appropriate transducer). As would be understood by those in the art, an electromechanical solenoid 200 is an actuator driven by electrical signals. The electromechanical solenoid actuator 200 translates electrical signals received from the microprocessor 205 into mechanical stimuli impacting the skin surface. More specifically, as further described herein, the solenoid 200 is a micro-solenoid that converts the electrical signals into magnetic impulses that physically drive a weight or membrane 215 ("the stimulator") to act upon the skin of the wearer. In some implementations, the stimulator 215 is insulated with a rubberized or plastic envelope, for purposes of noise abatement and user comfort.

It will be appreciated that the stimulator 215 can be fixedly attached to the solenoid 200 itself such that movement of the solenoid 200 results in direct translation (movement) of the stimulator 215. In at least some embodiments, the stimulator 215 can be in the form of a skin that surrounds and intimately contacts the solenoid 200. Movement of the solenoid 200 (as when energized) causes movement of the surrounding or adjacent stimulator 215 (membrane).

One or more light emitting devices 221 (e.g., LED) can also be operatively connected to the microprocessor 205. The LED 221 serves to output information to the user relevant to the operation of the ULF device 100 such as, a device status (e.g., on/off, active/inactive, battery level) and the like. By way of further example, the LED 221 can emit light pulses in synchrony with the stimuli being applied by the UHF device 100.

The display 222 (e.g., LCD display) can also be operatively connected to the microprocessor 205. The display 222 can be a digital display such as a segment display, a dot matrix display or a 2-dimensional display and can incorporate, by way of example and not limitation, a liquid crystal display, light emitting diode display, electroluminescent display and the like. The display 222 provides an output to the user of information relevant to the operation of the ULF device 100, such as the status of the device 100, operating parameters of the device local time, a second time zone, the date, and so on, as a function of the mode of the watch as managed by instructions executing in the microprocessor 205. By way of further example, the display 222 can display the frequency, amplitude and timer functions relating to the stimuli being applied by the UHF device, and related control features. The display 222 can also display the selected time period for application of the stimuli and optionally show a running time indicating the amount of time left for a given application. The time period can vary depending upon the application and can be on the order of less than 1 hr., less than 30 minutes, less than 20 minutes, less than 10 minutes, etc. The foregoing is not an exhaustive list of treatment time periods.

The timer function can be incorporated into the microprocessor 205 and is configured to keep track of time and more particular, the microprocessor 205 includes timers and counters. As the name implies, timers can tell the time and count. Counting and timing allows for some really cool things, like controlling the brightness of LEDs, controlling the angle of servo shafts, receiving sensor data that transmit in PWM (Pulse Width Modulation—more on that in another tutorial), making a timer (like on the stove), or just simply adding a time variable to your microcontroller project. It is important to know that there is a clock inside (or outside) the microcontroller. In fact, all microcontrollers have clocks in them (or use one that resides outside of a microcontroller). Microcontrollers need clocks so the programs can be executed in rhythm with the clock. This is the basic function of microcontrollers. A basic instruction is processed when a tick from the clock passes. The microprocessor 205 can thus readily keep track of how long a sensor measurement is outside an acceptable range (e.g., is greater or less than a threshold value).

The control button and touch interface represent one or more user input devices that are operatively connected to the microprocessor 205. Such user input devices serve to facilitate the capture commands from the user such as an on-off commands and operating parameters related to the operation of the device, for example, the frequency and amplitude of the tactile stimuli and the duration that the stimuli is administered and other such parameters as further described herein. User input devices can also serve to facilitate the capture of other information from the user and provide the information to the microprocessor.

The control button can be one or more switch(es), button(s), knob(s), key(s). The touch interface is a touch sensitive device that can be placed in register on the top of the display or on/around the perimeter of the display or anywhere on the housing. A touch interface is comprised of one or more thin, transparent layers that can detect when and where a user touches the interface and it allows a user to interact directly with what is displayed without requiring an intermediate device such as a computer mouse. The touch interface can be constructed using, by way of example and not limited to, resistive, capacitive, acoustic, infrared, optical imaging, or dispersive signal technology.

By way of further example, the touch interface and display can be integrated into a touch screen display. Accordingly, the screen is used to show a graphical user interface, which can display various fields or virtual buttons that allow for the entry of information by the user. Touching the touch screen at locations corresponding to the display of a graphical user interface allows the person to interact with the device to enter data, change settings, control functions, etc. So, when the touch screen is touched, interface communicates this change to microprocessor, and settings can be changed or user entered information can be captured and stored in the memory.

The communication interface 230 can also be operatively connected to the microprocessor 205. The communication interface 230 can be any interface that enables communication between the ULF device 100 and external devices, machines and/or elements including a user's computer system. Communication interface 230 can include but is not limited to a Bluetooth, or cellular transceiver, a radio transceiver, an NFC transceiver, a satellite communication transmitter/receiver, an optical port and/or any other such interfaces for wirelessly connecting the ULF device to an external computing device, such as a tablet, laptop, etc.

It can be appreciated that aspects of the present systems and methods can take the form of an entirely hardware embodiment, an entirely software embodiment (including firmware, resident software, micro-code, etc.), or an embodiment combining software and hardware. One of skill in the art can appreciate that a software process can be transformed into an equivalent hardware structure, and a hardware structure can itself be transformed into an equivalent software process. Thus, the selection of a hardware implementation versus a software implementation is one of design choice and left to the implementer. For example, the microcontroller can take the form of a circuit system, an application specific integrated circuit (ASIC), a programmable logic device, or some other suitable type of hardware configured to perform a number of operations. With a programmable logic device, the device is configured to perform the number of operations. The device can be reconfigured at a later time or can be permanently configured to perform the number of operations. Examples of programmable logic devices include, for example, a programmable logic array, programmable array logic, a field programmable logic array, a field programmable gate array, and other suitable hardware devices. With this type of implementation, software modules can be omitted because the processes for the different embodiments are implemented in a hardware unit.

To augment the neural recruitment of the tactile stimuli generated by the device 100, other stimuli may be paired with them, among them: light, sound, and electro-physiological impulses.

Figure 8A:
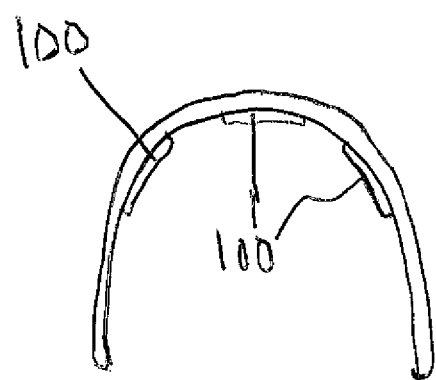
FIGS. 8A-8C depict various accessories that can carry the ULF device.
Figure 8B:
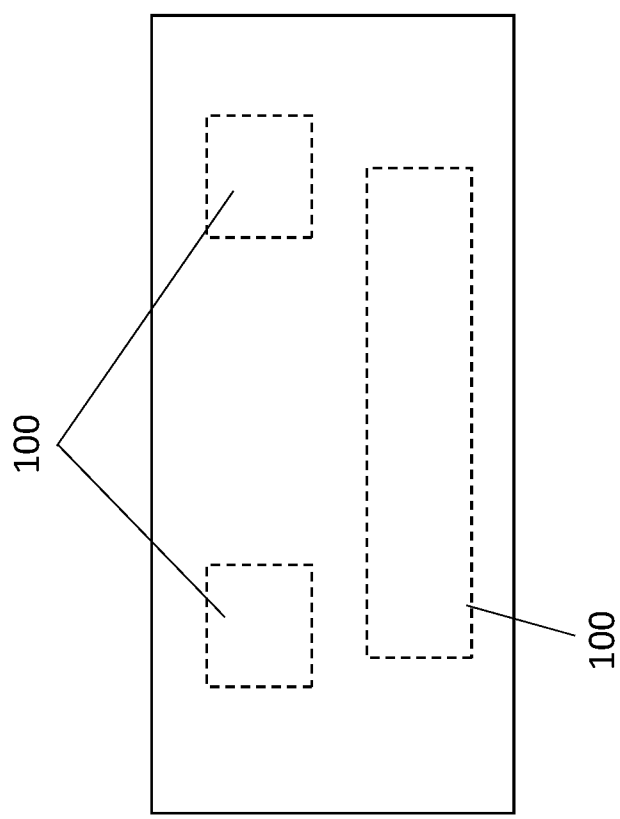

The ultra-low frequency device 100 can be apposed to the skin surface anywhere on the body, and different designs make it possible to appose the device to the wrists—as in a wristband format (see FIGS. 1-3)—or to the ankle, chest, abdomen, and to the head itself, as in a headband (FIG. 8A).

In one embodiment, the low-frequency stimuli generated and delivered by the device 100 can have an amplitude that is selected between about 0.5 mm to about 5 mm (e.g., between about 0.5 mm to about 3 mm). However, the aforementioned values are only exemplary in nature and not limiting of the present invention since depending upon the construction of the device 100 and/or the application, other amplitudes may be selected.

It will be understood that the device 100 is powered by a battery, which drives a microprocessor 205. The microprocessor can be programmed to vary the frequency of the impulses to the solenoid actuator. Frequencies may range from 2 Hz, to 0.1 Hz. The microprocessor may be programmed to vary the amplitude, or power of the stimuli, from subliminal levels to clearly perceptible levels. Programmable, as well, is a timer that shuts off the device, or that turns it on at a future time.

The actuator translates the signals from the microprocessor into mechanical stimuli impacting the skin surface. A micro-solenoid 200 converts the electrical signals into magnetic impulses, driving a weight or membrane to act upon the skin. The stimulator is insulated with a rubberized or plastic envelope, for purposes of noise abatement and subject comfort.

As described herein, the other visible component can be an LED that emits light pulses in synchrony with the stimuli; an LCD (liquid crystal display) to display frequency, amplitude and timer functions, and control buttons.

Operation and Modulation of ULF Stimuli based on Sensor(s) Measurements

In accordance with the present invention, the system 10 is configured for feedback modulation of stimuli delivered by the ULF devices 100, based on physiological data emitted by the subject. Modulation of the ULF tactile stimuli may include their frequency, pacing and rhythm—regular or irregular—amplitude, and timing of delivery.

As described in detail herein, the system 10 incorporates such biofeedback capabilities and more specifically and according to one example, one or more specialized sensors 300 are configured to relay information to the ULF device 100 on physiological parameters that measure states of activation, movement, anxiety and/or stress. These sensors 300 include but are not limited to:

Sensors for bodily motion and movement, such as accelerators.
Sensors for electro-dermal activity (EDA), that measure anxiety/tension/stress reactions.
Sensors for pulse rate.
Sensors for skin temperature
Sensors for blood pressure.
Sensors for muscular tension.
Sensors for electroencephalographic activity (EEG).
Sensors for respiratory rate.
Sensors for gastro-intestinal activity.
Sensors for bladder activity.

These sensors are described in more detail below.

Figure 5:
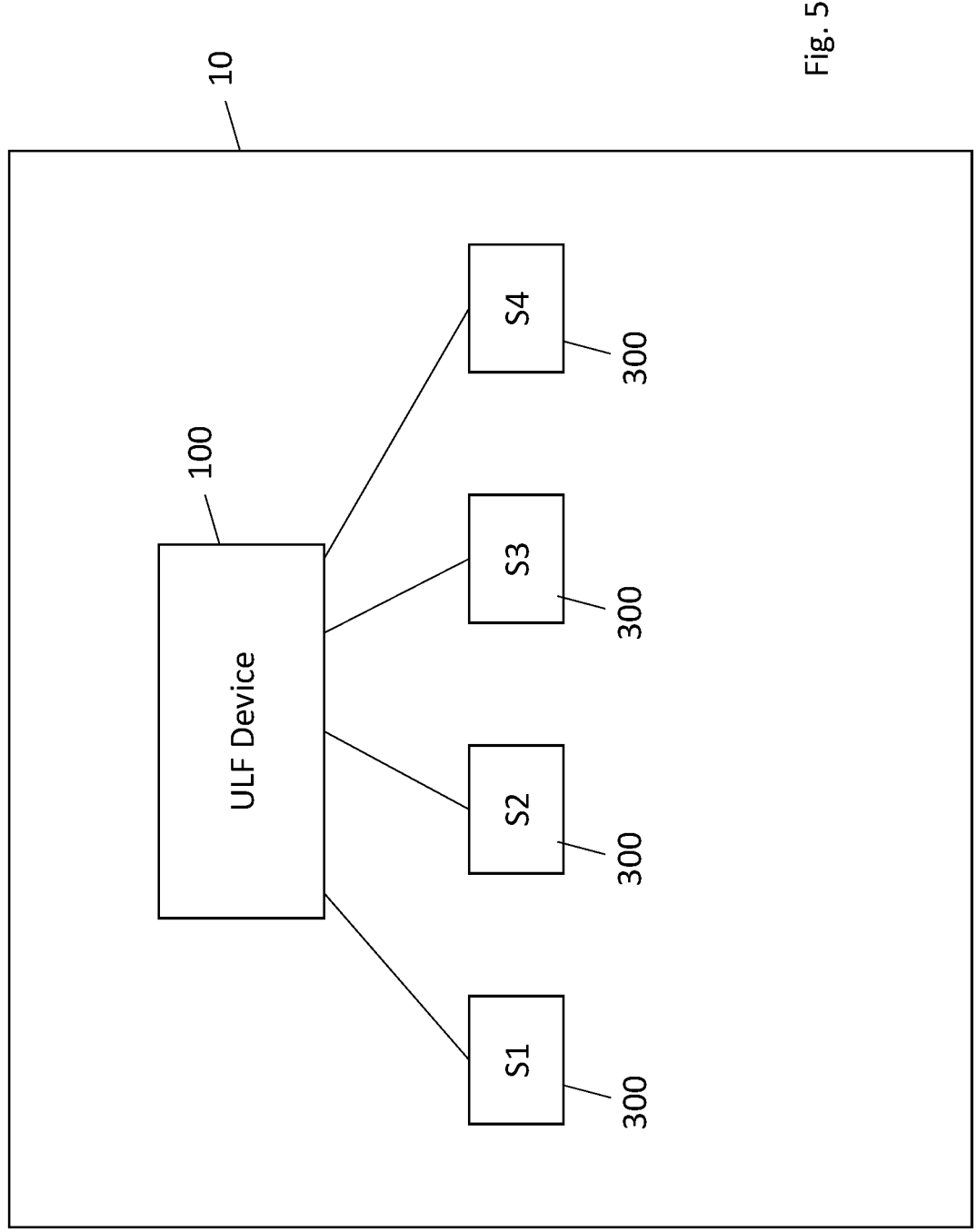
FIG. 5 is a block diagram showing a system in accordance with the present invention that includes an ULF device and one or more sensors.

As described herein, FIG. 5 depicts the system 10 as including the device 100 in communication with a plurality of sensors which can be represented as S1, S2, S3, S4, etc. It will also be understood that while FIG. 4 depicts only one device 100, there can be more than one device 100 as part of the system.

Stimuli Emitted by the ULF Device

Rhythmical or paced presentation of stimuli are different from vibratory stimulation. Vibration, according to Webster's Dictionary represents: "a periodic motion of the particles of an elastic body or medium in alternately opposite directions from the position of equilibrium when that equilibrium has been disturbed." The ULF device 100 teaches the presentation of ultra-low frequency rhythmic or paced stimuli to the skin which, according to definition of vibration, are not vibratory, because they neither have a periodic motion, nor do they have a point of equilibrium. Moreover, they are of such low frequency that they lie below the lower ranges for what is commonly conceived as vibrational.

Although the pulses delivered by ULF devices 100 are non-vibratory, the pulse itself may be generated by short bursts of vibrational energy. The important distinction is that the pulses themselves respect the ultra-low frequency ranges. A pulse thus experienced will not be experienced as a vibration, but rather as a single stimulus. A single pulse stimulus may thus be created by vibrational energy which may span into level referred to as ultrasonic, namely that which is beyond human hearing (greater than 20 kHz), or, as in medical ultrasound, in the range of 1 to 20 MHz.

The present refinement teaches the accrued capacity of the ULF device 100 for receiving any number of physiological data emitted by the subject, with a view to trigger, or modify the ULF tactile signal's relative to their onset, their frequencies, their pacing—regular or irregular—their force or amplitude, and their timing of delivery. Predicated on the physiological data received, the ULF devices 100 can thus be endowed with mechanisms for initiating corrective actions, e.g., the normalization of cardiovascular functions.

Delivery of ULF

As described herein, the device 100 is configured to deliver ultra-low stimuli is via electro-mechanical devices that incorporate solenoids or transducers.

Solenoids are essentially electro-magnets and in the case of the present invention are miniature electro-magnets adapted to mammalian tissue physiology which in their simplest form consists of coils of magnetic wire and a central moveable core that responds to electric current. Transducers are devices that convert one form of energy to another. They translate physical quantities, such as sound pressure and brightness into electrical signals or vice versa.

The properties inherent in this technology is that solenoids and transducers have the capacity to deliver ultra-low frequency repetitive stimuli, rhythmical or irregularly paced, while other methods, including those that rely on offset rotating motors to produce vibrations, cannot. Solenoid electromagnetic technology, for example, can thus deliver impulses to the body that range far below the Delta brain wave frequencies, the lower limit of Delta being 0.5 Hz. The impulses generated by solenoid technology can be programmed to frequencies as low as 0.1 Hz (or one stimulus every 10 seconds), and lower.

To augment the neural recruitment of the tactile stimuli, other stimuli may be paired with them, among them: light, sound, ultrasound, electro-magnetic, and electro-physiological impulses.

As described herein, the ULF device 100 can contact the skin surface anywhere on the body, and different designs make it possible to appose the device to the wrists—as in a wristband format—to the ankle, chest, abdomen, spine, and to the head itself, as in a headband.

A user wishing to normalize heart rate and blood pressure may choose to take cardiac function readings before using the device. The device is set at a frequency and amplitude that is indicated by a chart, predicated on the readings.

The device may incorporate a pulse sensor and/or a blood pressure sensor whose readings are shown on a display. Certain models may display respiratory rate.

Physiological Sensors

Augmentation of capacities for the ULF device 100 include sensors 300 activated by a subject's physiological signals. They in turn trigger the ULF device 100 to corrective action (which can be 1) initiation of stimuli deliver; 2) modulation (modification) of the stimuli currently being delivered; or 3) stopping the delivery of stimuli). In most instances, the sensors 300 detect a physiological overactivity and the ULF devices 100 are triggered to manifest their calming influence.

The microprocessor 205 can be configured to modulate the delivered stimuli based on feedback received from the at least one sensor 300. For example, if the recorded pulse rate (at rest) is substantially higher than the inputted target of say 75 bpm, then the microprocessor 205 can signal the ULF device to begin operation in a coaxing mode (in which the stimulus is presented with a lower frequency than the desired physiological response, so that the said desired response is attained more quickly) and then as the measured pulse rate begins to drop and reaches a threshold (reduced pulse rate), the microprocessor 205 then signals the ULF device 100 to operate in an entrainment mode of operation in which the stimulus frequency is applied corresponding to the desired response. The threshold at which the operating modes are switched depends in part on the initial recorded measurements from the sensor and other considerations. In one example, for a measured pulse rate that exceeds the threshold, the coaxing mode of operation can apply stimuli with a frequency of about 1.5 Hz and then for entrainment mode of operation, the frequency is lowered to 1 Hz. For example, the coaxing mode of operation can be used until the measured sensor data is within 20%, 15% or 10% of the target value. As an example, if the target value for pulse rate is 75 bpm (rest), coaxing can be used until the measured pulse rate is within 10% of the target value (i.e., when the measurement is at 82.5 bpm), then entrainment mode of operation is initiated. At a selection of 20%, the entrainment mode of operation is initiated when the pulse rate is at 90 bpm). In the event that the initial measurement (initial pulse rate) is not above the selected threshold percentage (e.g., 20%), then the microprocessor 205 can select a lower default percentage (such as 10%). For example, as mentioned above, at 20% selection, entrainment would begin at 90 bpm; however, if the initial pulse rate is less than 90 bpm (such as 88 bpm), then the microprocessor 205 can default to a 10% percentage and the coaxing mode of operation is used to bring down the pulse rate from the initial reading of 88 bpm to 82.5 bpm (10% value) and then entrainment is used to bring it to 75 bpm.

The present invention is thus directed, at least in part, to the inclusion of physiological sensors 300 in the ULF devices 100 whose purpose is to measure:

1. Physiological processes such as bodily motion, pulse rate, electro-dermal activity (EDA), body temperature, respiratory rate, blood pressure, electroencephalographic (EEG) activity, and/or intestinal and bladder activity.
2. These sensors may recruit various technologies.
3. Bodily movement sensors, for example, may include accelerometers.
4. Temperature sensors may include resistance temperature detectors (RTD) or negative temperature coefficient (NTC) thermistors, among others.
5. Electro-dermal activity (EDA) sensors measure skin resistance.
6. Pulse rate sensors usually utilize optoelectronic technology, and this by pairing light emitting diodes (LED) with a light dependent resistor (LDR), and a microprocessor.
7. As sensors detect undue activation of selected bodily functions, the engagement of the ULF device is triggered, thus offering soothing pacing down via its ULF stimuli, until such time that, once calming has been achieved, they can be discontinued.

ULF Device Sensors for Bodily Motion During Sleep Stages and During Meditation

The ULF device 100, in one embodiment, can be equipped with sensors 300 capable of detecting bodily motions. Such motions, when registered during sleep stages, may indicate any number of possibilities including imminent awakening, restless leg syndrome episodes, somnambulism and nightmares, among others. The controls of the ULF device 100 thus allow the user to set the operating mode to sleep mode.

Alerted by movement sensors 300, the ULF device 100 can then be prompted to action, delivering calming signals to the sleeper. The same principle applies to meditation practice, or to relaxation training.

Body motion sensors 300 generally derive their data from accelerators, which transfer changes in rates of motion to electrical data. Relayed to the ULF device's microprocessor 205, this information may be processed to activate the device's modulating signals, leading to the calming of kinetic activity.

One type of sensor for detecting motion is an accelerometer. An accelerometer is an electromechanical device that will measure acceleration forces. These forces may be static, like the constant force of gravity pulling at your feet, or they could be dynamic—caused by moving or vibrating the accelerometer. An accelerometer is thus a device that measures the vibration, or acceleration of motion of a structure. The force caused by vibration or a change in motion (acceleration) causes the mass to "squeeze" the piezoelectric material which produces an electrical charge that is proportional to the force exerted upon it. Since the charge is proportional to the force, and the mass is a constant, then the charge is also proportional to the acceleration.

There are two types of piezoelectric accelerometers (vibration sensors). The first type is a "high impedance" charge output accelerometer. In this type of accelerometer, the piezoelectric crystal produces an electrical charge which is connected directly to the measurement instruments. The charge output requires special accommodations and instrumentation most commonly found in research facilities. This type of accelerometer is also used in high temperature applications (>120 C) where low impedance models cannot be used.

The second type of accelerometer is a low impedance output accelerometer. A low impedance accelerometer has a charge accelerometer as its front end but has a tiny built-in micro-circuit and FET transistor that converts that charge into a low impedance voltage that can easily interface with standard instrumentation. This type of accelerometer is commonly used in industry.

Thus, when the user sets the ULF device 100 to operate on sleep mode, the controller (microprocessor 205) monitors the data (signals) from the accelerometer and if the detected motion (signal) exceeds a threshold value, the microprocessor 205 instructs the device 100 to deliver stimuli either for a set period of time or until the values (signals) from the accelerometer drop below the threshold value.

ULF Device Sensors for Electro-Dermal Activity (EDA)

Skin electrical conductivity has long been appreciated to reflect on sympathetic nervous system activation. Stress, anxiety, panic, will all lead to the exudation of dermal fluids which increase electrical conductivity. Formally known, as galvanic skin response (GSR), EDA, in a variation of this invention, may be measured via sensors that measure skin resistance, and relayed to the ULF device 100.

GSR originates from the autonomic activation of sweat glands in the skin. The sweating on hands and feet is triggered by emotional stimulation: Whenever we are emotionally aroused, the GSR data shows distinctive patterns that are visible with bare eyes and that can be quantified statistically.

With minimal preparation times and cleanup, skin conductivity is recorded non-invasively using two electrodes placed on the skin. This renders GSR measurements a lot more comfortable for respondents compared to other neuro-methods such as fMRI or EEG, where longer preparation and calibration phases are quite common (and sometimes a true hassle).

Generally, GSR sensors have a 1 cm$^2$ measurement site made of Ag/AgCl (silver/silver-chloride) and are placed either in reusable snap-on hook-and-loop straps or in a patch sticker. While the former can be applied as-is, the patch sticker requires to use conductive gel in order to improve the conductivity between skin and electrode.

The logic behind GSR is very simple and can be readily understood with review of the following steps: (1) place two electrodes on emotionally sensitive locations on the body; (2) apply a low constant voltage; (3) measure the voltage difference between the two electrodes; and (4) report the associated skin conductance.

As shown in FIG. 7, GSR thus typically consist of two electrodes 301, an amplifier 303 (to boost signal amplitude), and a digitizer 305 (to transfer the analog raw signal into binary data streams). Wireless GSR devices further contain data transmission modules 307 for communication with the recording computer (using the Bluetooth protocol, for example). Principally, GSR devices offer different sensor placement options. While some devices allow arbitrary sensor placements in any of the locations we have already mentioned, other devices have GSR electrodes rigidly mounted in wristbands or elastic straps.

As GSR measurements work by detecting the changes in electrical (ionic) activity resulting from changes in sweat gland activity, the electrodes must be sensitive to these changes, and able to transmit that information to the recording device. Most modern GSR electrodes have an Ag/AgCl (silver-chloride) contact point with the skin. Ag/AgCl electrodes are used as they are cheap, robust, safe for human contact, and of course are able to accurately transmit the signal from the ionic activity. Some electrodes also come prepackaged with ionic gel that can increase the signal fidelity, or ionic gel can be applied to achieve the same effect. Either way, the signal is sent through the electrode, to the wire (usually lead) that passes the information to the GSR device. From here the data is either stored within the device to be later uploaded, is transmitted wirelessly to a computer system, or the signal is sent through a further wired connection to a computer. Different GSR sensors allow different means of transmission, and the choice of each will depend on the kind of research you're carrying out.

Thus, EDA is the property of the human body that causes continuous variation in the electrical characteristics of the skin. Historically, EDA has also been known as skin conductance, galvanic skin response (GSR), electrodermal response (EDR), psychogalvanic reflex (PGR), skin conductance response (SCR), and skin conductance level (SCL). Human extremities, including fingers, palms, and soles of feet display different bio-electrical phenomena. IX-GSR, is a GSR meter (or a skin conductance meter) which displays the change electrical conductance between two points over time.

In an interpretation of this invention, the EDA sensor 300 is placed on the subject's skin to record electro-dermal activity. With an uptick of said activity, indicating stress, the sensor 300 alerts the ULF device 100 (once the electro-dermal activity exceeds a threshold value) in order to deliver commensurate calming ultra-low frequency tactile signals. As with the other sensors 300 described herein, the tactile signals (stimuli) are delivered until the electro-dermal activity falls back below the threshold value.

ULF Device Sensors for Skin Temperature

The ULF device 100 can also be in communication with a skin temperature probe (sensor) 300. Any number of different skin temperature sensors 300 can be used. As is known, a skin temperature probe is a highly accurate skin sensor for patient's surface temperature readings. The skin temperature probe can be a patch that include a pressure sensitive adhesive for attaching to the skin. A wire runs from the patch to the ULF device 100 so that the readings of the skin temperature probe are delivered to the processor (controller) of the ULF device 100. In this manner, the ULF controller receives input from the temperature probe and is configured to control the operation of the ULF device 100 and in particular, the administration of the stimuli.

Variations in skin temperature, under stable conditions, are often related to levels of sympathetic nervous system activity. Anxiety, tension and stress tend to constrict skin arterioles thus lowering skin temperatures. Thus, stress and anxiety states can manifest themselves in regional temperature fluctuations. Due to vasoconstriction, temperature of the hands and feet are observed to fall in states of tension. Input from the one or more temperature sensors 300 into the ULF device 100, for example, signaling the tense subject that hand readings are around 94° F. as an example. The ULF signals, now activated and combined with meditation on bodily warmth, maintain the ULF signals till hand temperatures attain desired levels (e.g., 96° F.), that correlate with generalized relaxation.

Accordingly, in one variation of the ULF device 100, a temperature sensor 300 is apposed to the skin surface and its electrical input is integrated into its microprocessor 205 functions. As skin temperature decreases are detected, indicating increased sympathetic nervous system activity, microprocessor 205 response allows for the delivery of calming ultra-low frequency stimuli. In the example noted above, the microprocessor 205 can thus be programmed so that it continuously monitors the temperature of the body, such as the hands at which the sensor 300 is located and in the event that the observed temperature falls below a target threshold (lower threshold), such as below 94° F., the microcontroller 200 initiates the operation of the ULF device 100 and the delivery of stimuli. The stimuli from the ULF device 100 can be continued until another threshold (upper threshold) is reached such as measuring a temperature at least greater than a target value, such as 96° F. Once this upper threshold is reached, the ULF device 100 can be turned off and the delivery of stimuli ceases. In another embodiment, the ULF device 100 can turn off when an increase in temperature within a range is achieved. For example, depending upon the first recorded temperature, the ULF device 100 can be turned off when an increase of greater than a certain value, such as a measured 2 to 4° F. increase in temperature, is observed.

Relationship Between Pulse Rate, Blood Pressure, Respiratory Rate and Oxygen Sensor Pulse rate, blood pressure and respiratory rate do not share strict linear relationships. In other words, a reduction in pulse rate or respiratory rate may not necessarily result in a commensurate drop in blood pressure, and vice versa. Yet, they are related. They all have a common denominator, namely the generalized appeasement of the organism's cardio-pulmonary and systemic physiological activation.

The function of these interdependent physiologic parameters is centralized in atavistic nervous system centers common to all mammals, namely the medulla oblongada and the brain stem, which oversee fundamental vegetative functions. Extensive dynamic neuronal cross-connections make these functions interdependent.

Slowdown in any one of these parameters will signal the eventual slowdown of the others. Well-known, for example, are the effects of deep slow breathing, especially if it is imbued with awareness. Sentient deep slow breathing will reflexly bring about a decrease in blood pressure and a slowdown of heart rate; it will also improve gas exchange and increase blood oxygen saturation.

Admixed with these parameters is the dimension of anxiety, one of the greatest contributors to cardio-vascular-pulmonary over-activity. The slow paced ULF stimuli serve to center attention away from intra-psychic anxiogenic concerns and onto a physical ULF message that beckons pan-systemic slowdown.

Pulse Rate Sensor

Sensors for pulse rate can be easily integrated into the workings of the system 10 and the ULF device 100. Pulse rate is usually measured via optoelectronic technology, and this by pairing light emitting diodes (LED) with a light dependent resistor (LDR), and a microprocessor.

To measure the heart rate, the heat beat/pulse is detected and the pulses are count for one minute to get the beats per minute. In order to detect the pulse, light passes light (using an LED) from one side of the finger and the intensity of light received on the other side (using an LDR) is measured. Whenever the heart pumps blood more, the light is absorbed by increased blood cells and we will observe a decrease in the intensity of light received on the LDR. As a result, the resistance value of the LDR increases. This variation in resistance is converted into voltage variation using a signal conditioning circuit usually an OP-AMP. The signal is amplified enough to be detectable by the microcontroller inputs. The microcontroller 200 can be programmed to receive an interrupt for every pulse detected and count the number of interrupts or pulses in a minute. The count value of pulses per minute will give you the heart rate in bpm (beats per minute). Alternatively, to save time, only the number of pulses for ten seconds are counted and then multiplied by 6 to get pulse count for 60 seconds/1 minute.

Information from the pulse rate sensor is relayed to the ULF device, which in turn is programmed to respond to heart rate parameters. If, for example, heart rate exceeds a certain threshold, the ULF device 100 will be commanded to begin its appeasement signals so that the heart rate will be entrained to set a slower pace.

The ULF stimuli emitted by the device 100 may thus be used to decrease pulse rate. The range of the cardiac device's output spans from 1.5 Hz, (reflecting the higher range limits of normal heart rate, namely 90 beats per minute), to 0.2 Hz, or one stimulus per 5 seconds, which coaxes heart rate to 0.2 Hz, or one stimulus per 5 seconds, which coaxes pulse rate to normalize more quickly. A cardiac rhythm sensor may be connected to the user that displays the user's pulse rate on the device. This provides visual biofeedback of cardiac rhythm.

Athletes usually have resting pulse rates ranging from 50 to 60 beats per minute. Tachycardia is defined as rates at or exceeding 100 beats per minute. This is found in certain cardiac conditions and in some anxiety states. If, for example, the goal is to respect a maximum resting heart rate of 75 beats per minute, for example, the ULF device may be programmed to begin activation when its sensors detect a rate of 70 beats per minute or 75 bpm or other inputted value. The ULF device will not only bring to awareness the rise in heart rate via its tactile signals but will also provide its entrainment signals encouraging pulse rate slowdown and importantly, a regular pacing of cardiac rhythm.

Sensor for Respiratory Motion

The ULF device 100, in one embodiment of the invention, can be equipped with one or more sensors capable of detecting bodily motions, and specifically motions of the thoracic cage or chest wall. Accelerometers detect rate of change in motion. The construction and operation of accelerometers are described herein.

In an application of this feature, a motion sensor detects the to and fro of respirations (rising and lowering of chest), sending data to the microprocessor of the ULF device. Said respiration sensor may be apposed to the chest wall by anyone of several means. Sensors may, for example, be integrated into the fabric of a garment or under-garment, or may be connected to the chest wall via medical adhesive or suction cups.

The controller can be programmed to detect motion that is outside of an accepted range.

Alerted by movement sensors, the ULF device 100 may then be prompted to action. In detecting an acceleration of breathing movement, the ULF device microprocessor may then be triggered to start emitting pulses, which by their temperance, slow down internal rhythms to achieve a more restful state.

Respiratory motion sensors derive their data from accelerators, which transfer changes in rates of motion to electrical data. Relayed to the ULF device's microprocessor, this information may be processed to activate the device's signals, leading to the calming of respiratory activity.

Slower respirations correlate with deeper respirations. Focusing awareness on the ULF signals allows the user to achieve meditative appeasement and calm.

Sensor for Blood Pressure

Blood pressure sensor data may be integrated into the ULF device. While traditional blood pressure measurements required an uncomfortable cuff Blood pressure sensors are best tolerated if they are non-intrusive. New technology is spawning blood pressure sensors that can be apposed to skin surfaces without using compression devices. Pulse wave velocity technology and piezo-electric films give accurate blood pressure readings that can be transmitted to the ULF device. Undue elevations in blood pressure may then trigger the calming influence of the ULF stimuli.

As mentioned, current technology for measuring blood pressure is optical heart rate monitoring (OHRM) technology which can be integrated into a wearable device or structure that is laid over the skin. The technology behind OHRM was inherited from clinical pulse oximetry and relied on the so-called photoplethysmography principle (PPG). The simplicity of the approach is that one simply needed to illuminate the skin of the wrist via a light source and collect the light that had been scattered within the tissues by means of a photodiode placed on the skin. Because the collected light had been amplitude-modulated by the pulsation of skin arterioles, one could then extract information on heart rate from analysis of those PPG time series. A sensor 300 can thus be provided for blood pressure measurement and the sensor 300 can be incorporated into the ULF device 100 and/or be a standalone sensor that is in communication with the device 100.

In the event that the ULF device 100 is a bracelet or wrist band, it can include a small cuff that can inflate to measure systolic and diastolic pressure via the oscillometric method. A target blood pressure is 120 over 80 and in the event that the reading is more than 120 over 80 but less than 140 over 90, you are at the higher end of the normal range. If the reading is more than 140 over 90 then the ULF device 100 should be operated automatically by the controller unless the user is participating or just participated in exercise or other event explains the high reading. The above readings are meant to be normal, at rest readings.

Sensor for Blood Oxygen Saturation

Sensors that measure blood oxygen saturation depend on differential light absorption of hemoglobin in its oxygenated versus non-oxygenated state. Pulse oximetry embodies this process. More specifically, pulse oximetry is a noninvasive method for monitoring a person's oxygen saturation ($SO_2$). Though its reading of peripheral oxygen saturation ($SpO_2$) is not always identical to the more desirable reading of arterial oxygen saturation ($SaO_2$) from arterial blood gas analysis, the two are correlated well enough that the safe, convenient, noninvasive, inexpensive pulse oximetry method is valuable for measuring oxygen saturation in clinical use. In its most common (transmissive) application mode, a sensor device (sensor 300) is placed on a thin part of the patient's body, usually a fingertip or earlobe, or in the case of an infant, across a foot. The device passes two wavelengths of light through the body part to a photodetector. It measures the changing absorbance at each of the wavelengths, allowing it to determine the absorbances due to the pulsing arterial blood alone, excluding venous blood, skin, bone, muscle, fat, and (in most cases) nail polish.

Depending on data from oximetry sensors 300, the ULF device 100 may be triggered to action (deliver of signals), signaling a therapeutic change in breathing pattern. Whereas fast shallow breathing favors low oxygen blood saturation, slow deep breathing encourages lung volume turnover.

Normal pulse oximeter readings usually range from 95 to 100 percent. Values under 90 percent are considered low and will cause the ULF device controller to operate and deliver stimuli.

Electroencephalogram (EEG) Sensor

The ULF device 100 can easily be adapted to integrate and respond to brain wave data. When worn somewhere on the head where proximity makes possible the recording of cortical electrical activity, the device is adapted to receive EEG data. These may limit themselves to a plurality of sensors 300, such as three electrodes, as in a one unit, or can take can number of other forms. As is known, electroencephalography (EEG) is an electrophysiological monitoring method to record electrical activity of the brain. It is typically noninvasive, with the electrodes placed along the scalp.

As is known, the brain emits a vast array of electrical waves whose configurations depend on a multitude of factors, physiologic and psychological. Technologies that modify brain wave can be used therapeutically to encourage healthy bodily responses. This invention centers on the induction of slow brain waves for their association with physiological rest and relaxation. Brain wave sensors 300 feed their data to the ULF device 100 in a subject who, for example, is interested in entering greater relaxation with its connected lower blood pressure, lower pulse rate, and reduced respiratory rate. The ULF device 100 can, in this example be programmed to deliver its entrainment signals as it detects EEG readings indicative of alertness, such as Beta waves (12 Hz to 30 Hz), or even Gamma (30 Hz and above) and to continue until the EEG shows an Alpha state (8 Hz to 12 Hz). In this example the ULF device 100 would be activated when EEG readings show a preponderance of Beta waves and maintain its therapeutic work until showing an Alpha preponderance. In other words, the microprocessor 205 can be configured such that when it detects that greater than 50% of the wave frequencies recorded by the EEG sensors 300 have wave frequencies greater than 12 Hz (i.e., the majority of the waves are Beta waves or even Gamma waves), the ULF device 100 administers the stimuli to the person until the data from the sensors 300 indicates that greater than 50% of the wave frequencies are Alpha waves. The trigger points of the microprocessor 205 can readily be changed as an input in that instead of a trigger of 50%, the trigger can be 66% or even 75%. In other words, when the trigger input is set at 66%, the ULF device 100 is not operated to deliver the stimuli until more than 66% of the wave frequencies are greater than 12 Hz.

The EEG sensors 300 can be incorporated into a headband or similar type structure that is configured to be worn around the head.

Respiratory Rate

Sensors 300 for respiratory rate are easily integrated into the workings of the ULF device 100.

Figure 8C:
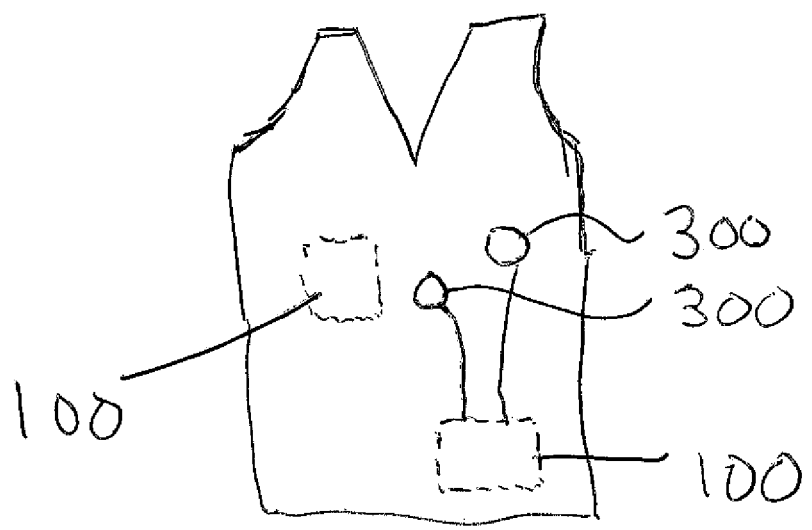

The sensor 300 measures the deflections of the chest and the gut that occur during breathing to directly measure respiratory rate. The sensor 300 is configured to convert and output the breathing deflections to the microprocessor 205 as varying low voltage signal when the sensor 300 is applied to the person's skin. The sensor 300 can be a single use sensor (disposable) that is part of a patch or the like that has an adhesive layer for attaching the sensor 300 to the skin. The patch can be connected to the microprocessor 205 as by a wire (that connects to a jack or the like in the ULF device body 110) or the connection can be wireless and some communication protocol, such as Bluetooth, can be used for transmitting the recorded data (measurements) from the sensor 300 to the microprocessor 205 and device 100. Instead of taking a patch form, the one or more sensors 300 can be incorporated into a vest or other article to be worn by the user or can be incorporated into a strap or band that can be worn around the chest of the user (See, FIG. 8C).

The microprocessor 205 processes the breathing signal using state of the art algorithms, which remove noise that is typically associated with other than breathing artefact such as walking or changing body position. This processed signal can be delivered to the display or to an external computing device, such as a tablet computer, where software displays accurate measurements of respiratory rate.

A median healthy respiratory rate centers around 12 breaths per minute. Increased rates are often observed in anxiety states. The ULF device 100 may receive data on breathing rate via chest stretch sensors. The ULF device may, for example, be triggered when the respiratory rate exceeds a threshold, such as 16 breaths/per minute, in which case the ULF device 100 will not only elicit awareness to this rise, but also encourage a respiratory rate slowdown with emission of its paced signals (stimuli). In this case, the signals (stimuli) will still range from 1 Hz to 2 Hz because the aim is to encourage a systemic body-wide physiological slowdown. The microprocessor can be configured such that it discontinues application of the stimuli (paced signals) when the respiratory rate falls below the threshold and remains below for a target amount of time that is input by the user. For example, the microprocessor 205 can be programmed such that the respiratory rate must remain below the threshold value for at least several minutes (e.g., at least two minutes) or some other amount of time before it then discontinues delivery of the stimuli.

Bladder Activity Sensor

The sensor 300 can be used to monitor bladder activity. In particular, electromyography uses special sensors to measure the electrical activity of the muscles and nerves in and around the bladder and the sphincters. The sensors 300 are placed on the skin near the urethra and rectum or on a urethral or rectal catheter. Muscle and nerve activity is recorded and delivered to the ULF device 100. In the event that the sensor 300 detects electrical activity that exceeds a threshold value, the stimuli can be delivered as a result of control of the at least one electro-mechanical device by the controller.

Operation of the Microprocessor 205

Similar to the other sensors 300, the controller of the ULF device 100 can be configured to initiate operation and delivery of stimuli when the output from the skin temperature probe exceeds a threshold value.

It will also be appreciated that the controller of the ULF device 100 can be configured that operation is not initiated unless two or more sensors are outside of the accepted ranges (values) for the respective sensors. For example, if the output of the skin temperature probe exceeds a threshold value, the controller of the ULF device 100 can be configured such that it does not initiate delivery of the stimuli unless the output from at least one other sensor is outside of its acceptable range. In this sense, the system 10 can be designed so that some of the sensors 300 are designated as primary sensors and other sensors 300 are designated as secondary sensors. The controller of the ULF device 100 can be configured such that when output from a designated secondary sensor lies outside an accepted range, the controller will not initiate delivery of the stimuli unless output from a primary sensor lies outside an accepted range. Alternatively, the controller can be programmed such that if the output of a secondary sensor lies significantly outside the accepted range, e.g., greater than 25%, greater than 50% or greater than 100%, then the controller will initiate delivery of the stimuli based only on the measurements of the secondary sensor without regard to whether the measurements of the primary sensor are outside an acceptable range.

In one embodiment, a GSR/EDA sensor 300 is paired with a pulse rate sensor 300 and the pulse rate sensor 300 is designated as the primary sensor, while the GSR/EDA sensor 300 is designated as the secondary sensor.

In another embodiment, one EEG sensor 300 is paired with a pulse rate sensor 300 and the pulse rate sensor is designated as the primary sensor and the EEG sensor 300 is designated as the secondary sensor.

In other embodiments, all of the sensors 300 are treated as primary sensors and if any one of the outputs from any one of the sensors 300 exceeds a threshold value (e.g., is outside an accepted range), the controller signals operation of the ULF device 100 and delivery of the stimuli.

Kit

Figure 6:
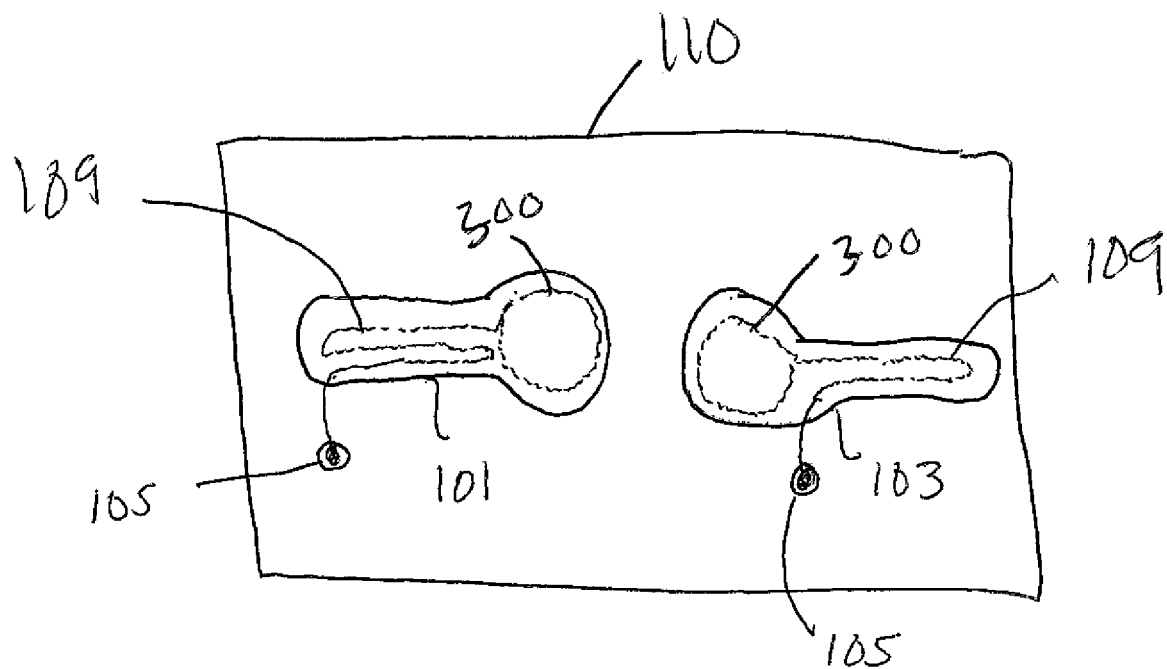
FIG. 6 is a plan view of an exemplary ULF device with a housing that includes one or more recessed portions that receive sensors and wiring.

It will be appreciated that the system 10 can be supplied in a kit form. For example, and as shown in FIG. 6, when the device 100 is paired with one or more sensors 300, the housing of the device 100 (e.g., the top surface) can include one or more recessed portions 101, 103 that hold the one or more sensors 300. Thus, when the sensor 300 is in the form of a skin patch or the like, the recessed portion 101, 103 can be sized to receive and hold the sensor 300 along with any wiring 109. In this way, the system 10 is compact and easy to transport. A fastener, such as a strap or the like, can be used to hold the sensor 300 and wire within the recessed portion 101, 103.

The housing of the device 100 can also have one or more jacks 105 or the like for receiving a plug at the end of the sensor wire to establish connection between the sensor 300 and the ULF device 100.

Alternatively, as mentioned, the one or more sensors 300 can communicate with the ULF device 100 in a wireless manner.

In accordance with one embodiment, the system 10 of the present invention offers one or more of the following features:

1. The present invention concerns the augmented capabilities for devices that have been granted patents as follows: U.S. Pat. No. 9,610,421 B2 "Devices and Methods Utilizing Ultra-Low Frequency Non-Vibratory Tactile Stimulation for Regulation of Physiological Processes; and Canada: Serial No 2,733,972 "Vibrational Delta and Theta Brain Wave Induction Apparatus and Method for Stimulation of Sleep."

A USPTO patent application U.S. Ser. No. 11/075,075 was submitted in 2005 and entitled, "Vibrational Delta and Theta Brain Wave Induction Apparatus and Method for the Stimulation of Sleep."

2. Devices described in these patents are referred to as ULF (ultra-low frequency) devices because they emit ultra-low tactile stimuli, of sufficient amplitude and in proper timing, to influence physiological mechanisms in human and mammals.

3. In addition to humans, the present invention may be adapted to veterinary use. Animals, domestic and other, may benefit from the physiological slowdown and modulating effects of the described ULF technology.

4. The innovations proposed center on the normalization of cardiovascular and cardiopulmonary functions by ULF technology. Sensors gather data on body functions, relaying them to ULF device microprocessors, which in turn drive actuators imparting signals to the nervous system.
5. The ULF devices emit stimuli at frequencies that are ultra-low. For purposes of describing this invention, ultra-low frequencies herewith referred to belong in a range of 2 Hz (two per second) to 0.1 Hz (or one stimulus every 10 seconds).
6. ULF device stimuli are non-vibrational in that they are independently generated and programed by microprocessors that drive solenoid or transducer actuators. These in turn activate membranes apposed to the skin, anywhere on the body, with intensity, however minimal, to engage the response of skin sensory receptors.
7. The present invention teaches the presentation of ultra-low frequency rhythmic or non-rhythmic stimuli to the skin that are, according to definitions of vibration, not vibratory, because they neither have a periodic motion, nor do they have a point of equilibrium. Moreover, they are of such low frequency that they lie below the lower ranges for what is commonly conceived as vibrational.
8. Although the ULF pulses are non-vibratory, each individual pulse may consist of short bursts of vibrational energy. The important distinction is that the pulses themselves respect ultra-low frequency ranges. A pulse thus generated will not be experienced as a vibration, but rather as a single stimulus. A single pulse stimulus may therefore be created by the single impact of a solenoid actuator, or be created by vibrational energy.
9. Pulses created by vibrational energy may use vibrations in the sub-acoustic range (less than 20 Hz), the acoustic range (20 to 20,000 Hz), but also may include ranges referred to as ultrasonic, namely that which is beyond human hearing (greater than 20 kHz); or, as in medical ultrasound, in the range of 1 to 20 MHz.
10. The ULF device signals may be fixed—in regard to rate, amplitude and duration and timing of delivery—and predicated on the condition to be modulated. Modification of these parameters may be available via controls on the ULF device itself. Or, they may be provided by remote controlled Blue Tooth technology
11. The ULF stimuli engage peripheral nervous system neurons that, in turn, influence central nervous system (CNS) functions. The CNS has myriad connections to physiological processes and rhythms, including, but not limited to: cardio-vascular functions such as pulse rate and blood pressure, brain wave generation, circadian rhythms, emotional states, stress responses, and muscular tension.
12. The physiological and neurological principles invoked are called entrainment and prompting. A rhythmic stimulus will, under these physiological laws, promote synchronous physiological and neurological responses. In the present invention, the physiological and neurological principles invoked are called entrainment and prompting. A rhythmic stimulus will, under these physiological laws, promote synchronous physiological and neurological responses. If, for example, the therapeutic goal is to guide pulse rate down to 70 beats per minute from a higher level, the device would be set at that rate, and via tactile entrainment, it would eventually reach the desired rate.
13. Another phenomenon can be called physiological coaxing. In this phenomenon, a stimulus may be presented with a much lower frequency than the desired physiological response, so that the said desired response is attained more quickly. In the same example above, the device would be set at 60 Hz, in order to bring it down to 70 Hz faster.
14. The present invention proposes devices and methods for modulating cardiovascular functions utilizing tactile stimuli that entrain the nervous system. There is a relationship between pulse rate, blood pressure, respiratory rate, and blood oxygen saturation. In the case of hypertension, the device entrains the nervous system to relax the intensity and frequency of its signals to the vasculature. The invention's fundamental concept is that tactile ULF stimuli have the capacity to modulate, via nervous system circuitry, the pace of the heartbeat, the tonicity of the body vasculature, the respiratory rate, and consequently, the blood oxygen saturation.
15. In the main embodiment of the proposed invention, pulse rate data is fed to the ULF device microprocessor. Sensors for pulse rate use optoelectronic technology by pairing light emitting diodes (LED) with a light dependent resistor (LDR) and a microprocessor.
16. Information from the pulse rate sensor is programmed to respond to heart rate parameters. If, for example, heart rate exceeds a certain threshold, the ULF device will begin its appeasement signals so that the heart rate becomes entrained to assume a slower pace. Cardiovascular activation may need to be curtailed during sleep for any number of reasons, including proclivity to strokes. The ULF device could thus detect unwanted cardiovascular activation and promptly address it by way of its soothing signals.
17. The ULF stimuli emitted by the device may thus be used to selectively decrease pulse rate. Concomitantly, they appease blood pressure elevations and lower respiratory rate.
18. The range of the cardio-pulmonary device's output spans from 2 Hz, or two cycles per second, to 0.1 Hz, or one stimulus per 10 seconds, which coaxes pulse rate to normalize more quickly. A pulse rate ULF device may display the user's pulse rate, providing useful visual feedback of cardiac rhythm's slowdown.
19. In one embodiment of the invention, the ULF device is equipped with sensors capable of detecting motions of the thoracic cage or chest wall. Accelerometers detect rate of change in motion. In one embodiment of the ULF device, sensors for respiratory rate provide the ULF microprocessor with data about breathing activity. Respiratory hyperactivity can be an indicator for the anxiety/stress spectrum and can negatively impact cardiovascular readings. Sensors for respiratory rate are easily integrated into the workings of the ULF device if the ULF device is worn so that chest movements activate incorporated accelerometers. The ULF stimuli emitted by the device may be used to regulate respiratory rate and rhythm, as in the treatment of certain types of hyperventilation.
20. In an application of this feature, a motion sensor detects the to and fro of respirations, sending data to the microprocessor of the ULF device. Said respiration sensor may be apposed to the chest wall by anyone of several means. Sensors may, for example, be integrated into the fabric of a garment or under-garment, or may be connected to the chest wall via medical adhesive or suction cups.
21. Alerted by movement sensors, the ULF device may then be prompted to action. In detecting an acceleration of breathing movement, the ULF device microprocessor may then be triggered to start emitting pulses, which by their temperance, slow down internal rhythms to achieve a more restful state.

Respiratory motion sensors derive their data from accelerators, which transfer changes in rates of motion to electrical data. Relayed to the ULF device's microprocessor, this information may be processed to activate the device's signals, leading to the calming of respiratory activity. Slower respirations correlate with deeper respirations. Focusing awareness on the ULF signals allows the user to achieve meditative appeasement and calm.

22. In one embodiment of the ULF device, blood pressure sensors transmit their data to the ULF microprocessor. Blood pressure can be gauged non-invasively by using pulse wave velocity technology. Exceeding parameters that indicate a movement toward hypertensive ranges, the ULF device may then be triggered to exert calming influence, which will slow down pulse rate and ease off blood pressure.

23. In one embodiment of the ULF device, sensors for bodily motion are integrated into its capacities. Cardiovascular tension can be accompanied by agitation, especially during sleep phases. In this adaptation of the invention, the ULF device is equipped with one or more accelerometers that respond to variations in bodily movements. This capacity, for example, is useful in gleaning information on restlessness during sleep where increasing body motions may be an indication of imminent waking, of anxiety during sleep as in nightmares, of impending somnambulism, or of restless legs activity.

In detecting acceleration of movement, the ULF device may then be triggered to start emitting pulses that appease cardiovascular activation.

24. In one embodiment of the invention calls for ULF device sensors for sympathetic nervous system activity pointing to anxiety and/or stress reactions, because they contribute to cardiovascular and cardio-respiratory dysfunction. Sensors for physiological correlates of anxiety include changes in electro-dermal activity (EDA), changes in skin temperature, or changes in muscular activity, as in agitation. ULF devices receiving such data can be invited to respond accordingly.

25. In one embodiment of the ULF device, sensors for skin temperature provide data for variations that indicate the presence of anxiety and stress. Sensors may include resistance temperature detectors (RTD), or negative temperature coefficient (NTC) thermistors, among others. Fluctuations in skin temperature, under stable conditions, are often related to levels of sympathetic nervous system activity. Anxiety, tension and stress tend to constrict skin arterioles thus lowering skin temperatures. In this variation of the ULF device, a temperature sensor is apposed to the skin surface and its data is integrated into its microprocessor functions. As sudden skin temperature decreases are detected during sleep, indicating increased sympathetic nervous system activity and increased cardiovascular activation, ULF microprocessor response allows for the timely delivery of calming ultra-low frequency stimuli.

26. In one embodiment of the ULF device, sensors for electro-dermal activity (EDA) are integrated into its feedback functions. Electro-dermal activity (EDA), measures the sympathetic system's output. Said activity is part of a global physiological state that identifies with psychic tension, anxiety and stress that contribute to cardiovascular dysfunction. Skin sweat glands are activated in sympathetic nervous system discharge and their discharges increase skin electrical conductivity.

EDA—formally referred to as galvanic skin resistance (GSR)—has long been used to measure general anxiety levels. In anxiety states, stemming from any one of a number of etiologies, skin resistance to electrical conduction is decreased. EDA can easily be integrated into the ULF device. As the device detects an uptick in sympathetic activity, and therefore anxiety, the ULF device can be programmed to trigger its calming stimuli in a timely fashion.

27. In one embodiment of the ULF device, sensors for electroencephalographic (EEG) data feed into the ULF microprocessor. Cardiovascular activation can be associated with certain brain wave activation patterns, such as higher Beta, and Gamma brainwaves. The ULF device thus can be adapted to integrate and respond to brain wave data. Sensors are worn where proximity makes possible the recording of cortical electrical activity, such as the head.

28. Batteries power the ULF devices. They drive microprocessors that regulate several functions. The most fundamental function is the frequency function, which ranges from 2 Hz to 0.1 Hz. The microprocessor can also be programmed to vary the amplitude, or force of the stimuli, from subliminal to clearly perceptible levels. Programmable, as well, are on/off timing functions.

29. While stimuli are generally presented at regular intervals, the present invention also makes possible the presentation of stimuli at irregular, or at patterned frequencies, or at gradually decreasing, or increasing frequencies and amplitudes.

30. The solenoid actuator translates the signals from the microprocessor into mechanical stimuli impacting skin surfaces. The micro-solenoid converts the electrical signals into magnetic impulses, driving a weight to act upon the skin. A rubberized or plastic membrane surrounds the actuator for purposes of noise abatement, and for enhancing subject comfort.

31. ULF cardiovascular devices may be applied to the skin surface anywhere on the body via any number of designs. One such variation includes a wristband configuration. Other designs make it possible for the ULF devices to be connected to the ankle, the chest, the abdomen, and the head, among others.

32. The device's effectiveness is enhanced by techniques of concentration, visualization, and meditation. By directing mindful attention to the experience of ULF stimuli, the programming of the nervous system is accelerated and desired physiological responses are more efficiently achieved. With repeated use of the device, its stimuli come to be established as conditioned reflexes that, with subsequent presentation, automatically induce their beneficial physiological effects.

33. ULF stimuli, under the scope of this invention, may be other than mechanical. Skin receptors exist for vibration, heat, cold, pain, and electric current—direct and alternating—as well as for magnetism and ultrasound. This invention, other than mechanically stimulating pressure dermal and sub-dermal sensory receptors, may recruit ULF stimuli utilizing electro-physiological, electro-magnetic, and/or ultrasound energies.

34. To augment the neural recruitment of the tactile stimuli, other auxiliary stimuli may be paired with them, among them: light, sound, ultrasound, electromagnetic, and electro-physiological impulses.

35. Addressed by the ULF device is the dimension of anxiety, one of the greatest contributors to cardio-vascular-pulmonary over-activity. The slow paced ULF stimuli serve to center attention away from intra-psychic anxiogenic concerns and onto a tactile and/or other physical ULF message that beckons pan-systemic slowdown.

36. The ULF stimuli engage peripheral nervous system neurons which, in turn, engage central nervous system (CNS) functions. The CNS has myriad connections to physiological processes and rhythms, including, but not limited to: cardio-vascular functions; brain waves and brain metabolism; sleep/wake functions; stress responses; emotional states, and muscular tension.

37. As sensors detect undue activation of selected bodily functions which may indicate unwanted cardiovascular-pulmonary comportment, the engagement of the ULF device is triggered, thus offering physiological pacing down via its ULF stimuli, until such time that, once calming has been achieved, they can be discontinued.

38. Physiological processes such as bodily motion, electroencephalographic (EEG) activity, pulse rate, respiratory rate, blood pressure, electro-dermal activity (EDA), and body temperature, may all be relevant to the evaluation and to the modification of cardiovascular functions.

39. The ULF device's calming signals may be fixed—in regard to rate, amplitude and timing of delivery; or they may be predicated on the data provided by sensors and the parameters programmed by the micro-processor. Modification of these parameters may be available via controls on the ULF device itself. Alternatively, they may be provided by remotely controlled Blue Tooth technology.

40. Batteries, driving microprocessors that regulate several functions, power the ULF devices. The most fundamental function is the frequency function, which ranges from 2 Hz to 0.1 Hz. The microprocessors can be programmed to select their output to the actuators. Stimuli amplitude, or power of the stimuli, is adjusted from subliminal to clearly perceptible levels. Programmable, as well, is a timer that shuts off the device, or that turns it on at a future time.

41. While stimuli are generally presented at regular intervals, the present invention also makes possible the presentation of stimuli at irregular, or at patterned frequencies, or at gradually decreasing, or increasing frequencies.

42. The micro-solenoid actuator translates signals from the microprocessor into mechanical stimuli impacting skin surfaces. The solenoid converts the electrical signals into magnetic impulses, driving a weight to act upon the skin. A rubberized or plastic membrane dampens the impact of the actuator for purposes of noise abatement, and for enhancing subject comfort.

43. The ULF microprocessor may drive different modalities of stimuli, either individually, or in combination. To augment neural recruitment of tactile stimuli, other stimuli modalities may be paired synchronously with them, namely: light, sound, ultrasound, electro-magnetic, and electro-physiological impulses. The ULF device could thus offer, in addition to tactile stimuli, audio, visual, and/or electro-physiological entrainment.

44. Via the increased resonance of nervous system networks, multimodal stimuli enhance the capacity of the ULF device to regulate physiological processes such as blood pressure and heart rate. Examples are light, sound, ultrasound, electro-magnetic, and electro-physiological impulses. The ULF device could thus offer, in addition to tactile stimuli, audio, visual, and/or electro-physiological entrainment, as follows:

45. Sounds. The rhythm frequency may, in addition to tactile stimuli, generate anyone of a number of sounds, or tones. A menu of pleasing sounds may be chosen such as waterfalls, waves, musical instruments, or electronically generated sounds.

46. Light. The microprocessor may drive mini-lights. An LED (light emitting diode) or other light source, capable of being perceived by the user, even through closed eyelids, may be incorporated in the device. Color preferences may be selected.

47. Electrophysiological stimulation. The microprocessor may drive an electrophysiological stimulation unit (ESU) that emits micro-currents, below the threshold of perception, or ones barely perceptible so as not to be distracting. These micro-currents, delivered via electroconductive electrodes enhance the tactile stimuli's effects. Amperage, measured in microamperes (mA), may range from 1 to 100 mA. Electrical pulse width may range up to 500 microseconds ($\mu$s).

48. In addition to the above, the ULF device may deliver other energies to the body which may not have clearly defined receptors, but which nevertheless have biological effects. Ultra-low frequency parameters are respected in this embodiment. The energies include:

49. Magnetic energies. Pulsed micro-energy electromagnetic stimuli can be delivered by the ULF microprocessor, respecting ultra-low frequency parameters. This may be fruitful for medical research.

50. The ULF device, respecting ultra-low frequency parameters, may deliver ultrasound energies. This may be fruitful for medical research.

Notably, the figures and examples above are not meant to limit the scope of the present invention to a single embodiment, as other embodiments are possible by way of interchange of some or all of the described or illustrated elements. Moreover, where certain elements of the present invention can be partially or fully implemented using known components, only those portions of such known components that are necessary for an understanding of the present invention are described, and detailed descriptions of other portions of such known components are omitted so as not to obscure the invention. In the present specification, an embodiment showing a singular component should not necessarily be limited to other embodiments including a plurality of the same component, and vice-versa, unless explicitly stated otherwise herein. Moreover, applicants do not intend for any term in the specification or claims to be ascribed an uncommon or special meaning unless explicitly set forth as such. Further, the present invention encompasses present and future known equivalents to the known components referred to herein by way of illustration.

The foregoing description of the specific embodiments will so fully reveal the general nature of the invention that others can, by applying knowledge within the skill of the relevant art(s) (including the contents of the documents cited and incorporated by reference herein), readily modify and/or adapt for various applications such specific embodiments, without undue experimentation, without departing from the general concept of the present invention. Such adaptations and modifications are therefore intended to be within the meaning and range of equivalents of the disclosed embodiments, based on the teaching and guidance presented herein.

It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one skilled in the relevant art(s).

While various embodiments of the present invention have been described above, it should be understood that they have been presented by way of example, and not limitation. It would be apparent to one skilled in the relevant art(s) that various changes in form and detail could be made therein without departing from the spirit and scope of the invention. Thus, the present invention should not be limited by any of the above-described exemplary embodiments, but should be defined only in accordance with the following claims and their equivalents.

What is claimed is:

1. An apparatus configured to generate and apply mechanical stimuli to skin of a user for regulating a physiological process comprising:
   a housing having a first surface for placement against the skin;
   at least one electro-mechanical actuator provided along first surface and configured to generate and apply the mechanical stimuli to the skin;
   wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived;
   at least one sensor that is configured to monitor a physiological property of the user; and a controller that is in communication with the at least one electro-mechanical actuator and the at least one sensor and is configured to control operation of the at least one electro-mechanical actuator, in at least a first operating mode, based on measurements of the at least one sensor;
   wherein the one or more sensor is selected from the group consisting of: (1) a first sensor for detecting respiratory motion; (2) a second sensor for detecting blood pressure; and (3) a third sensor for detecting blood oxygen saturation.

2. The apparatus of claim 1, wherein the controller is configured such that when a measurement from one of the first sensor, second sensor, and third sensor exceeds a threshold value, the controller initiates operation of the at least one electro-mechanical actuator.

3. The apparatus of claim 1, wherein the one or more sensor comprises at least the first sensor which comprises an accelerometer that is incorporated into the housing and in communication with the controller, the controller initiates operation of the at least one electro-mechanical actuator when data from the accelerometer exceeds a threshold that is indicative of an excess change in motion in the sensor.

4. The apparatus of claim 1, wherein the second sensor includes a light source for illuminating skin of the user and a photodiode that collects light that has been scattered, the controller being further configured such if a measured pulse rate exceeds a threshold value, the controller initiates operation of the at least one electro-mechanical actuator.

5. The apparatus of claim 4, wherein the light source comprises an LED and the LED and photodiode are incorporated into the first surface of the housing.

6. The apparatus of claim 5, wherein the LED and photodiode are incorporated into a standalone sensor that is in communication with the controller either via a wire or wireless communication.

7. The apparatus of claim 1, wherein the third sensor is configured to pass two wavelengths of light through a body part of the user to a photodetector and the controller is configured to measure a changing absorbance at each of the two wavelengths, allowing the controller to determine the absorbances due to pulsing arterial blood alone.

8. The apparatus of claim 1, wherein the housing is incorporated into one of: an article of clothing, a belt, a headband, wristband, and an ankle bracelet.

9. The apparatus of claim 1, wherein the controller receives measurements from each of the first sensor, the second sensor and the third sensor.

10. The apparatus of claim 9, wherein the controller is configured such that the at least one electro-mechanical actuator is operated only when two or more of the first sensor, the second sensor and the third sensor exceed a respective threshold value.

11. The apparatus of claim 1, wherein the controller initiates operation of the at least one electro-mechanical actuator when a measurement from the second sensor is indicative of a blood pressure that is more than 140 over 90 (systolic/diastolic).

12. The apparatus of claim 11, wherein the pair of electrodes are incorporated into and are located along the first surface of the housing, the housing being flexible to allow the housing to curve and be placed on the skin of the stomach.

13. The apparatus of claim 1, wherein the controller initiates operation of the at least one electro-mechanical actuator when a measurement from the third sensor is a reading of less than 90 percent oxygen saturation.

14. The apparatus of claim 1, wherein the housing includes at least one open recessed compartment for receiving and holding the at least one sensor and any wiring.

15. The apparatus of claim 1, wherein the at least one sensor comprises at least the seventh sensor and includes a pair of electrodes that are configured to deliver signals to the controller.

16. The apparatus of claim 1, wherein the at least one sensor comprises at least one primary sensor and a secondary sensor and the controller is configured such that the controller only initiates operation of the at least one electro-mechanical actuator when the secondary sensor exceeds a threshold value by a prescribed percent or when the primary sensor also exceeds a threshold value.

17. The apparatus of claim 1, wherein the electro-mechanical actuator comprises an electro-mechanical solenoid.

18. The apparatus of claim 1, wherein the at least one sensor is disposed external to the housing; however, is in communication with the controller.

19. An apparatus configured to generate and apply mechanical stimuli to skin of a user for regulating a physiological process comprising:
   a housing having a first surface for placement against the skin;
   at least one electro-mechanical actuator provided along first surface and configured to generate and apply the mechanical stimuli to the skin;
   wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived;

at least one sensor that is configured to monitor a physiological property of the user; and a controller that is in communication with the at least one electro-mechanical actuator and the at least one sensor and is configured to control operation of the at least one electro-mechanical actuator, in at least a first operating mode, based on measurements of the at least one sensor;

wherein the one or more sensor is selected from the group consisting of: (1) a first sensor for detecting respiratory motion; (2) a second sensor for detecting blood pressure; and (3) a third sensor for detecting blood oxygen saturation;

wherein the at least one sensor comprises at least the sixth sensor for measuring gastro-intestinal activity and includes a pair of electrodes for placement on a stomach of the user and configured to deliver signals to the controller.

20. An apparatus configured to generate and apply mechanical stimuli to skin of a user for regulating a physiological process comprising:

a housing having a first surface for placement against the skin;

at least one electro-mechanical actuator provided along first surface and configured to generate and apply the mechanical stimuli to the skin;

wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived;

at least one sensor that is configured to monitor a physiological property of the user; and a controller that is in communication with the at least one electro-mechanical actuator and the at least one sensor and is configured to control operation of the at least one electro-mechanical actuator, in at least a first operating mode, based on measurements of the at least one sensor;

wherein the one or more sensor is selected from the group consisting of: (1) a first sensor for detecting respiratory motion; (2) a second sensor for detecting blood pressure; and (3) a third sensor for detecting blood oxygen saturation;

wherein the at least one electro-mechanical actuator comprises a solenoid that converts electrical signals from a processor into magnetic impulses that physically drive a weight or membrane to act upon the skin.

21. An apparatus configured to generate and apply mechanical stimuli to skin of a user for regulating a physiological process comprising:

a housing having a first surface for placement against the skin;

at least one electro-mechanical actuator provided along first surface and configured to generate and apply the mechanical stimuli to the skin;

wherein the mechanical stimuli comprise ultra-low frequency, non-vibratory stimuli that have a frequency between about 2 Hz (two stimuli per second) to about 0.1 Hz (one stimulus every 10 seconds), and wherein the mechanical stimuli have sufficient energy so as to engage skin sensory receptors that are configured to convey signals to the nervous system where the stimuli are at least one of consciously perceived and subliminally perceived;

at least one sensor that is configured to monitor a physiological property of the user; and a controller that is in communication with the at least one electro-mechanical actuator and the at least one sensor and is configured to control operation of the at least one electro-mechanical actuator, in at least a first operating mode, based on measurements of the at least one sensor;

wherein the one or more sensor is selected from the group consisting of: (1) a first sensor for detecting respiratory motion; (2) a second sensor for detecting blood pressure; and (3) a third sensor for detecting blood oxygen saturation;

wherein the controller is configured to initially instruct operation of the at least one electro-mechanical actuator in a coaxing mode of operation and then transition to an entrainment mode of operation based on measurements of the at least one sensor.

* * * * *